US009468454B2

(12) United States Patent
Johnson et al.

(10) Patent No.: US 9,468,454 B2
(45) Date of Patent: Oct. 18, 2016

(54) MOTOR CONTROL AND FEEDBACK IN POWERED SURGICAL DEVICES

(71) Applicant: Ethicon Endo-Surgery, Inc., Cincinnati, OH (US)

(72) Inventors: Eric N. Johnson, Maineville, OH (US); Kevin L. Houser, Springdale, OH (US); David C. Yates, West Chester, OH (US); Rudolph H. Nobis, Mason, OH (US); Chad P. Boudreaux, Cincinnati, OH (US); Gregory A. Trees, Loveland, OH (US); Geoffrey S. Strobl, Williamsburg, OH (US); Gavin M. Monson, Oxford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 229 days.

(21) Appl. No.: 14/166,133

(22) Filed: Jan. 28, 2014

(65) Prior Publication Data

US 2015/0209061 A1    Jul. 30, 2015

(51) Int. Cl.
*A61B 17/32*    (2006.01)
*A61B 18/14*    (2006.01)
(Continued)

(52) U.S. Cl.
CPC ... *A61B 17/320016* (2013.01); *A61B 18/1445* (2013.01); *A61B 17/32002* (2013.01); *A61B 34/76* (2016.02); *A61B 90/03* (2016.02);
(Continued)

(58) Field of Classification Search
CPC .............. A61B 17/28; A61B 17/2804; A61B 17/2812; A61B 17/2816; A61B 17/282; A61B 17/2833; A61B 17/2909; A61B 17/32; A61B 17/320016; A61B 17/2841; A61B 17/32002; A61B 2017/00017–2017/0003;
A61B 2017/00075; A61B 2017/00137; A61B 2017/00398; A61B 2017/2825; A61B 2017/2829; A61B 2017/2837; A61B 2017/2845; A61B 2017/2912; A61B 2017/2918; A61B 2017/2923; A61B 2017/2925; A61B 18/1442–18/1447; A61B 2018/1452–2018/1457; A61B 2019/464; A61B 2019/465–2019/466; A61F 9/00763
See application file for complete search history.

(56) References Cited

U.S. PATENT DOCUMENTS 5,077,506 A * 12/1991 Krause ............. A61B 17/32002
 318/67
5,903,117 A * 5/1999 Gregory ................... H02P 6/14
 318/400.09

(Continued)

FOREIGN PATENT DOCUMENTS

EP    2462878 A1    6/2012

OTHER PUBLICATIONS

International Search Report and Written Opinion for PCT/US2014/069115 mailed May 8, 2015 (18 pages).

*Primary Examiner* — David C Eastwood
(74) *Attorney, Agent, or Firm* — Mintz Levin Cohn Ferris Glovsky and Popeo, P.C.

(57) ABSTRACT

Surgical devices and methods are described herein that provide improved motor control and feedback, thereby combining advantages of manually-operated and powered surgical devices. In one embodiment, a surgical device includes a proximal handle portion that includes a motor, a distal end effector coupled to the handle portion, and a cutting element configured to cut tissue engaged by the end effector, wherein the motor is configured to supply power that moves the cutting element. The device also includes a motor control mechanism configured to cause the amount of the power to dynamically change in response to a manual user input when the cutting element is moving.

10 Claims, 26 Drawing Sheets

(51) Int. Cl.
 *A61B 17/00* (2006.01)
 *A61B 17/29* (2006.01)
 *A61B 18/00* (2006.01)

(52) U.S. Cl.
 CPC ............... *A61B2017/0042* (2013.01); *A61B 2017/00137* (2013.01); *A61B 2017/00398* (2013.01); *A61B 2017/2918* (2013.01); *A61B 2017/2925* (2013.01); *A61B 2018/00303* (2013.01); *A61B 2018/1455* (2013.01); *A61B 2090/064* (2016.02); *A61B 2090/0811* (2016.02)

(56) References Cited

U.S. PATENT DOCUMENTS

| | | | |
|---|---|---|---|
| 5,916,165 A * | 6/1999 | Duchon | A61M 5/14546 600/431 |
| 6,118,236 A * | 9/2000 | Shaw | D05B 69/18 112/271 |
| 7,776,037 B2 | 8/2010 | Odom | |
| 8,064,980 B2 * | 11/2011 | Lederer | A61B 5/7475 200/56 R |
| 8,128,625 B2 | 3/2012 | Odom | |
| 8,357,158 B2 | 1/2013 | McKenna et al. | |
| 8,357,160 B2 | 1/2013 | Odom | |
| 2006/0273135 A1 * | 12/2006 | Beetel | A61B 17/068 227/175.1 |
| 2007/0175949 A1 * | 8/2007 | Shelton, IV | A61B 17/07207 227/176.1 |
| 2007/0175957 A1 * | 8/2007 | Shelton, IV | A61B 17/07207 227/178.1 |
| 2007/0175958 A1 * | 8/2007 | Shelton, IV | A61B 17/07207 227/178.1 |
| 2007/0175962 A1 * | 8/2007 | Shelton, IV | A61B 17/07207 227/178.1 |
| 2007/0179476 A1 * | 8/2007 | Shelton, IV | A61B 17/07207 606/1 |
| 2008/0039836 A1 | 2/2008 | Odom et al. | |
| 2008/0078803 A1 * | 4/2008 | Shelton | A61B 17/0644 227/176.1 |
| 2008/0210738 A1 * | 9/2008 | Shelton | A61B 17/064 227/176.1 |
| 2008/0223904 A1 * | 9/2008 | Marczyk | A61B 17/07207 227/176.1 |
| 2008/0255607 A1 * | 10/2008 | Zemlok | A61B 17/07207 600/127 |
| 2009/0076534 A1 * | 3/2009 | Shelton, IV | A61B 17/07207 606/170 |
| 2009/0209979 A1 * | 8/2009 | Yates | A61B 17/07207 606/143 |
| 2009/0289096 A1 * | 11/2009 | Shelton, IV | A61B 17/07207 227/180.1 |
| 2010/0076474 A1 * | 3/2010 | Yates | A61B 17/07207 606/170 |
| 2010/0198220 A1 * | 8/2010 | Boudreaux | A61B 17/07207 606/52 |
| 2010/0200636 A1 * | 8/2010 | Zemlok | A61B 17/07207 227/175.1 |
| 2010/0217264 A1 | 8/2010 | Odom et al. | |
| 2011/0006101 A1 * | 1/2011 | Hall | A61B 17/07207 227/175.2 |
| 2011/0006103 A1 * | 1/2011 | Laurent | A61B 17/07207 227/176.1 |
| 2011/0011915 A1 * | 1/2011 | Shelton, IV | A61B 17/07207 227/176.1 |
| 2011/0034910 A1 * | 2/2011 | Ross | A61B 17/07207 606/1 |
| 2011/0087209 A1 * | 4/2011 | Boudreaux | A61B 18/085 606/29 |
| 2011/0288573 A1 | 11/2011 | Yates et al. | |
| 2011/0290856 A1 * | 12/2011 | Shelton, IV | A61B 17/320092 227/180.1 |
| 2012/0022525 A1 | 1/2012 | Dietz et al. | |
| 2012/0078139 A1 | 3/2012 | Aldridge et al. | |
| 2012/0116379 A1 * | 5/2012 | Yates | A61B 17/00234 606/33 |
| 2012/0116391 A1 | 5/2012 | Houser et al. | |
| 2012/0138658 A1 * | 6/2012 | Ullrich | A61B 17/072 227/175.1 |
| 2012/0265230 A1 * | 10/2012 | Yates | A61B 17/07207 606/170 |
| 2013/0060278 A1 * | 3/2013 | Bozung | A61B 17/1675 606/205 |

\* cited by examiner

MOTOR CONTROL AND FEEDBACK IN POWERED SURGICAL DEVICES

FIELD

The present invention relates to devices and methods for use in surgical procedures and, more particularly, to powered surgical devices and methods that provide improved motor control and feedback to a user.

BACKGROUND

Various surgical devices are known for compressing and cutting different types of tissue. In general, these devices have an end effector, such as a pair of opposed jaw members, that is configured to engage tissue and a cutting mechanism that is configured to sever tissue engaged by the end effector. Certain of these devices can also be configured to apply energy, such as radio frequency (RF) electrical energy, to the tissue disposed between the jaws. The application of electrical energy in the vicinity of a tissue cut can seal the cut to prevent bleeding of the tissue, leakage of other fluids through the cut, etc.

Many surgical devices used for compressing and cutting tissue are manually operated, such that a user has to provide an actuation force through, for example, a handle portion of a device coupled to the end effector. However, the forces required to operate such a device on thick or tough tissue can exceed the strength of some operators and may fatigue others. In an effort to address this problem, certain surgical devices include electric motors to provide the necessary actuation force. This reduces the amount of force required from a user, as the user need only actuate a button, switch, or other electrical actuation mechanism.

A common concern with electrically-powered surgical devices is the lack of control and tactile feedback that is inherent to a manually-operated device. Surgeons and other users accustomed to manually-operated devices often find that electrically-powered devices reduce their situational awareness because of the lack of feedback from the device. For example, electrically-powered devices do not provide users with any feedback regarding the progress of a cutting and/or sealing operation (e.g., an actuation button or switch is typically binary and provides no feedback on how much tissue has been cut, etc.) or the forces being encountered (e.g., toughness of the tissue). This lack of feedback can produce undesirable conditions. For example, if a motor's power is not adequate to compress and transect tissue the motor can stall out. Without any feedback to a user, the user may maintain power during a stall, resulting in excessive heating within the device. Furthermore, even if the stall is discovered, users often cannot correct the stall by reversing the motor to retract the cutting mechanism because a greater amount of force is available to advance a cutting mechanism than is available to reverse it (e.g., due to inertia when advancing). As a result, time-intensive extra operations can be required to free the stalled cutting element and disengage the device from the tissue.

In addition, electrically-powered devices can be less precise in operation than manually-operated devices. For example, users of manually-operated devices are able to instantly stop the progress of a cutting mechanism by simply releasing the actuation mechanism. With an electrically-powered device, however, releasing an actuation button or switch does not result in instantaneous halting of a cutting element, as the electric motor will continue to drive the cutting element until the kinetic energy of its moving components is dissipated. As a result, a cutting element may continue to advance for some amount of time even after a user releases an actuation button.

Still further, the introduction of motor controls in addition to controls for the delivery of RF or other energy to seal tissue can overwhelm an operator by requiring simultaneous management of multiple controls. Separate controls can be combined in certain devices to reduce the number that must be managed by a user, but this often reduces the control of the various functions that is possible by the operator.

Accordingly, there is a need in the art for improved devices and methods that provide greater control over, and feedback from, electrically-powered surgical devices.

SUMMARY

The devices and methods described herein address the aforementioned need by providing greater control over, and feedback from, the operation of a powered surgical device. The devices and methods described herein generally accomplish this by dynamically controlling the output of a motor based on a user input. In certain embodiments, the user input can be a pressure exerted on a trigger, switch, or other component of a surgical device being manipulated by a user. The surgical device can include a mechanism for detecting changes in the pressure exerted by the user, and dynamically adjusting an amount of power output by the motor in response thereto. In so doing, the devices and methods described herein provide a proportional link between the amount of force provided by a user and the amount of power provided by an electric motor. Further, the devices and methods described herein can be configured to provide tactile feedback to a user regarding the amount of power being output by the motor. Accordingly, a user's experience operating the device can be more similar to that of using a manually actuated instrument, but without the undesirable physical exertion required from the user to operate such a device.

In one aspect, a surgical device is provided that includes a proximal handle portion having a motor, and a distal end effector coupled to the proximal handle portion. The device further includes a cutting element configured to cut a tissue engaged by the end effector, and the motor is configured to supply power that moves the cutting element through the tissue. The device also includes a motor control mechanism configured to cause the amount of the power to dynamically change in response to a manual user input when the cutting element is moving.

The devices and methods described herein can include a number of additional features and/or variations, all of which are considered within the scope of the present invention. For example, there are a number of different configurations for the motor control mechanism. In certain embodiments, the motor control mechanism can include a potentiometer, and the amount of the power supplied by the motor can change if a voltage of the potentiometer does not match a predetermined reference voltage. Conversely, the amount of the power supplied by the motor can remain constant (i.e., not change) if the voltage of the potentiometer matches the predetermined reference voltage.

The motor control mechanism can be configured to perform in a variety of manners. For example, in some embodiments the motor control mechanism can be configured to immediately stop the motor from supplying the power when the manual user input ceases. In other embodiments, the motor control mechanism can be configured to increase the amount of the power supplied by the motor when the amount of the power supplied by the motor falls below a predetermined threshold amount until the amount of the power supplied by the motor is at least equal to the predetermined threshold amount. In still other embodiments, the motor control mechanism can be configured to increase the amount of power supplied by the motor in response to the manual user input increasing in pressure.

In other embodiments, the surgical device can include other components, such as a trigger coupled to the handle portion. The trigger can be configured to be actuated by the user, and actuation of the trigger can be configured to automatically actuate the motor control mechanism. In certain embodiments, the motor control mechanism can be configured to dynamically change the amount of the power provided to the motor so as to maintain a relationship between a position of the cutting element and a position of the trigger. In still other embodiments, the surgical device can include a feedback mechanism configured to provide a tactile feedback to the user. The tactile feedback can be representative of the amount of the power being supplied by the motor.

In another aspect, a surgical device is provided that includes a proximal handle portion that includes a motor, an elongate shaft extending distally from the handle portion, and an end effector at a distal end of the elongate shaft. The surgical device further includes a control element configured to actuate the motor in response to a user input of pressure thereto, the actuation of the motor being configured to move a cutting element configured to cut a tissue engaged by the end effector, and an amount of the pressure being proportional to an amount of power that is supplied by the motor.

As noted above, the surgical devices and methods described herein can include a number of variations, any or all of which can be combined with any of the various embodiments described herein. For example, in some embodiments the surgical device can include a potentiometer configured to be actuated in response to the user input of pressure. When the potentiometer is actuated, the power supplied by the motor can change if a voltage of the potentiometer does not match a predetermined reference voltage, and the power supplied by the motor can remain constant (i.e., not change) if the voltage of the potentiometer matches the predetermined reference voltage. In certain embodiments, the surgical device can further include a switch configured to be actuated in response to the user input of pressure, and the potentiometer can be configured to be actuated in response to the user input of pressure only after the switch is actuated.

In other embodiments, the motor can be configured to immediately stop supplying the power when the user input of pressure ceases. In still other embodiments, the amount of power supplied by the motor can be prevented from exceeding a first predetermined threshold amount of power when the cutting element is moving proximally and is prevented from exceeding a second predetermined threshold amount of power when the cutting element is moving distally. In certain embodiments, the second predetermined threshold amount can be greater than the first predetermined threshold amount. Still further, in certain embodiments the amount of power supplied by the motor can be prevented from falling below a predetermined threshold amount of power when the cutting element is moving. In still other embodiments, the amount of power supplied by the motor can cause the movement of the cutting element to gradually accelerate at a predetermined rate.

In some embodiments, the control element can include at least one of a trigger and a pressure bladder. Regardless of what components are included in the control element, in some embodiments the amount of the pressure can be directly proportional to the amount of power supplied by the motor. In certain embodiments, the surgical device can also include an adjustment mechanism configured to be manually manipulated by a user so as to adjust a responsiveness of the motor to the user input of pressure.

In still other embodiments, the control element can be configured to provide a tactile feedback to the user when the pressure is being input, the tactile feedback being representative of the amount of the power supplied by the motor.

In another aspect, a surgical method is provided that includes engaging a tissue with an end effector of a surgical device, and causing a motor of the device to supply power to a cutting element of the device such that the cutting element moves through the tissue so as to cut the tissue. The method further includes causing an amount of the power supplied by the motor to dynamically change in response to a manual user input to the device when the cutting element is moving.

As with the surgical devices described above, there are a number of additional method steps, or variations thereof, that can be included in the surgical method. For example, in some embodiments the method can further include providing a tactile feedback to the user via the device, where the tactile feedback indicates the amount of the power. This and any other variation described herein or appreciated by one of skill in the art is considered within the scope of the present invention.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The present invention generally relates to devices and methods that provide improved motor control and feedback in powered surgical devices. As is explained in more detail below, the devices and methods described herein generally provide greater control by dynamically changing an amount of power output by a motor in response to a manual user input to the device. For example, in certain embodiments an amount of power output from a motor to drive a cutting element of a surgical device can dynamically vary such that it is directly proportional to a force applied to a trigger by a user. In other embodiments, an amount of power output from a motor can be varied so as to maintain a relationship between a position of a cutting element of a surgical device and a position of a trigger. Furthermore, the devices and methods described herein can provide increased tactile feedback to a user regarding the progress of a cutting (or other) operation, such that a user's experience is more similar to that of a manually-operated surgical device. The devices and methods described herein can provide users with an intuitive and responsive interface for controlling a powered surgical device.

Figure 1:
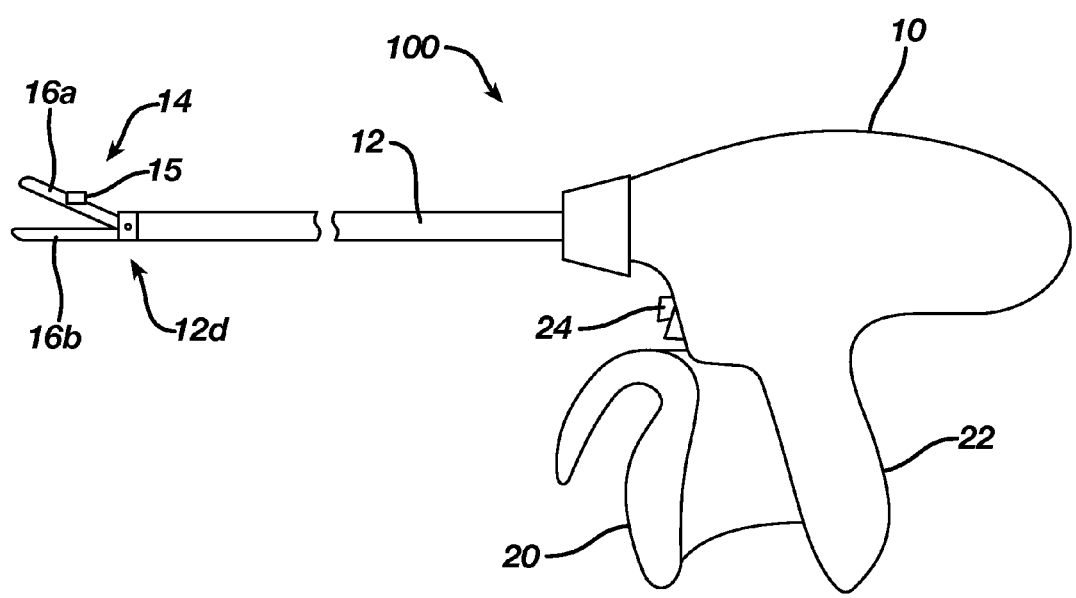
FIG. 1 is a side view illustration of one embodiment of a powered surgical device.

FIG. 1 illustrates one embodiment of a surgical device configured to grasp and cut tissue. A surgical device 100 can generally include a proximal handle portion 10, a shaft portion 12, and an end effector 14 for grasping tissue. The proximal handle portion 10 can be any type of pistol-grip or other type of handle known in the art that is configured to carry various actuators, such as actuator levers, triggers or sliders for actuating the end effector 14. In the illustrated embodiment, the proximal handle portion 10 includes a closure grip 20 and a stationary grip 22, and movement of the closure grip 20 toward and away from the stationary grip 22 adjusts a position of the end effector 14. The shaft portion 12 extends distally from the proximal handle portion and can have a bore (not shown) extending therethrough for carrying mechanisms for actuating the jaws.

Figure 2:
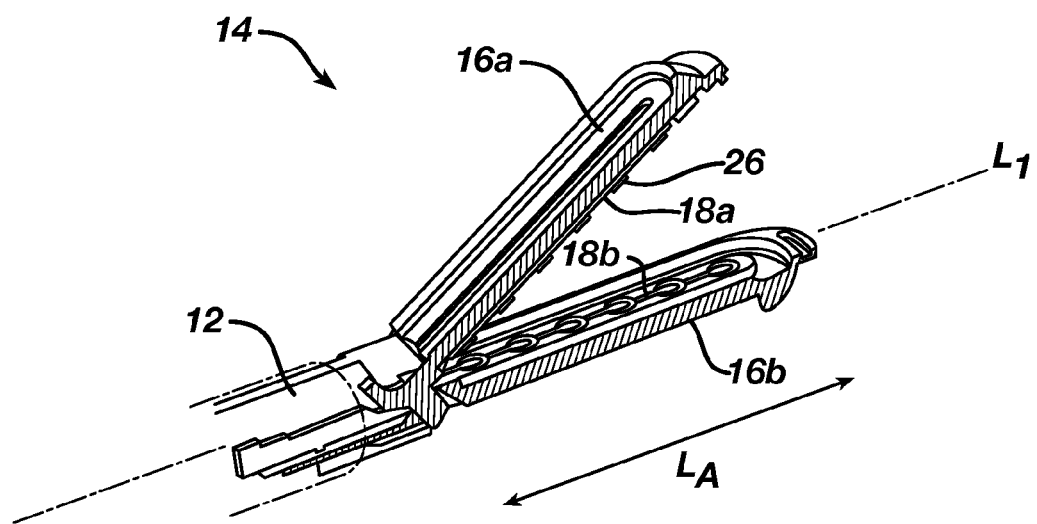
FIG. 2 is a perspective view illustration of the end effector of FIG. 1 in an open position.

The end effector can have a variety of sizes, shapes, and configurations. As shown in FIG. 1, the end effector 14 can include first and second jaws 16a, 16b disposed at a distal end 12d of the shaft portion 12. As can be seen in FIG. 2, the end effector 14 can include a first, upper jaw 16a and second, lower jaw 16b, one or both of which can be configured to close or approximate about an axis. Both of the jaws 16a, 16b can be moveable relative to the shaft portion 12 or alternatively a single jaw can rotate so that the end effector 14 can move between a first, open position in which the jaws 16a, 16b are positioned at a distance apart to a second, closed position in which the jaws 16a, 16b are moved toward one another and are substantially opposed. When the jaws 16a, 16b are in the second, closed position, a longitudinal axis of the upper jaw 16a can be substantially parallel to a longitudinal axis of the lower jaw 16b and the jaws 16a, 16b can be in direct contact. In the illustrated embodiment, the upper jaw 16a can pivot relative to the shaft portion 12 and relative to the lower jaw 16b while the lower jaw 16b remains stationary. In the illustrated embodiment, the jaws 16a, 16b have a substantially elongate and straight shape, but a person skilled in the art will appreciate that one or both of the jaws 16a, 16b can be curved along axis $L_1$. The jaws 16a, 16b can have any suitable axial length $L_A$ for engaging tissue, where the axial length A is measured along a longitudinal axis $L_1$ of the end effector 14, as shown in FIG. 2. The axial length A of the jaws 16a, 16b can also be selected based on the targeted anatomical structure for transection and/or sealing.

The jaws 16a, 16b can have any combination of features configured to facilitate grasping tissue therebetween. The first jaw 16a can have a first inner engagement surface 18a and the second jaw 16b can have a second inner engagement surface 18b, both of the first and second engagement surfaces 18a, 18b being configured to directly contact tissue. Either one or both of the engagement surfaces 18a, 18b can include one or more surface features formed thereon that can help secure the tissue thereon. For example, the surface features can include various surface features, such as teeth, ridges, or depressions, configured to increase friction between the tissue and the engagement surfaces 18a, 18b of the jaws 16a, 16b without tearing or otherwise damaging the tissue in contact with such surface features. FIG. 2 illustrates a plurality of teeth 26 positioned along an axial length of both of the engagement surfaces 18a, 18b and can facilitate grasping tissue and forming substantially smooth, uniform layers of tissue to improve tissue effect. The first and second jaws 16a, 16b can optionally include features for interacting with a compression member (not shown) configured to apply compressive forces on tissue. For example, the first and second jaws 16a, 16b include first and second recessed slots (not shown) that can receive portions of a compression member and act as a track to direct movement of the compression member. As another example, the first and second recessed slots can be configured to receive portions of a cutting member, as will be discussed in greater detail below.

Figure 3:
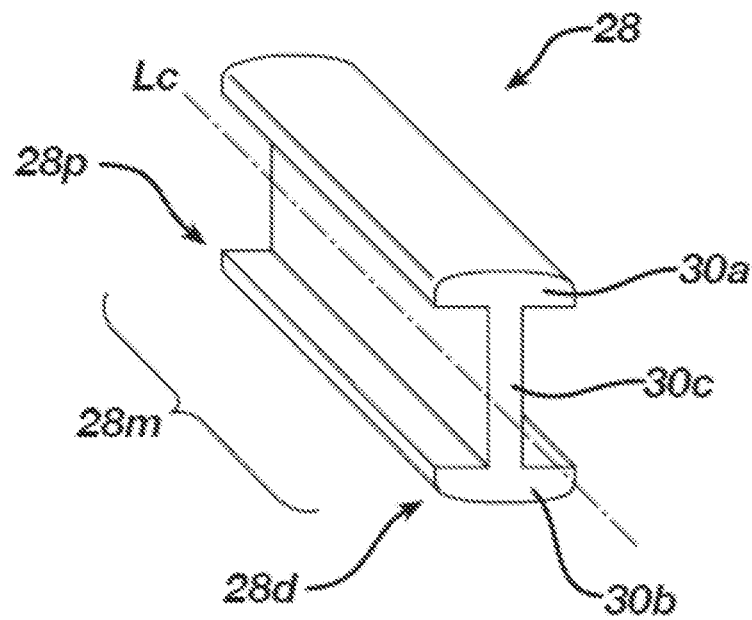
FIG. 3 is a perspective view illustration of one embodiment of a compression member configured to apply a compressive force on tissue.

A compression member can have various sizes, shapes, and configurations. In general, a compression member can have an elongate shape and can be moveable proximally and distally along the longitudinal axis $L_1$ of the end effector 14. An exemplary compression member 28 is illustrated in FIG. 3. As shown, the compression member 28 can have a proximal end 28p, a medial portion 28m, and a distal end 28d. The proximal end 28p and the medial portion 28m of the compression member 28 can be sized and shaped to reciprocate within the shaft portion 12 of the device 100, while the distal end 28d of the compression member 28 can be sized and shaped to interact with the jaws 16a, 16b of the end effector 14. A longitudinal axis $L_c$ of the compression member 28 can be aligned and coaxial with longitudinal axis $L_1$ of the end effector 14 and of the shaft portion 12, though other configurations are possible. The compression member 28 can be actuatable from the proximal handle portion of the instrument by any suitable mechanism that is operatively coupled to the proximal end 28p of the compression member 28, such as via the firing button 24 shown in FIG. 1. The compression member 28 can include a connecting portion 30c and upper and lower flanges 30a, 30b thus providing an "I-beam" type cross-sectional shape at the distal end 28d of the compression member 28. In the illustrated embodiment, the upper and lower flanges 30a, 30b are positioned substantially perpendicular to the connecting portion 30c to form the "I-beam" shape. As previously mentioned, the upper and lower flanges 30a, 30b can be sized and shaped to slide in the recessed slots in each of the upper and lower jaw 16a, 16b, and this sliding contact of lateral edges of the flanges 30a, 30b and sides of each of the recessed slot portions can prevent lateral flexing of the jaws 16a, 16b. The compression member 28 can have various other configurations. For example, the upper flange 30a can have a width that is greater than a width of the lower flange 30b, the widths being measured in a direction perpendicular to the longitudinal axis $L_1$ of the end effector 14. In addition, the upper and lower flanges 30a, 30b can extend along an entire length of the compression member 28, as shown in FIG. 3, or can extend along only a portion of a length of the compression member, e.g., only a distal portion of the compression member.

Figure 3A:
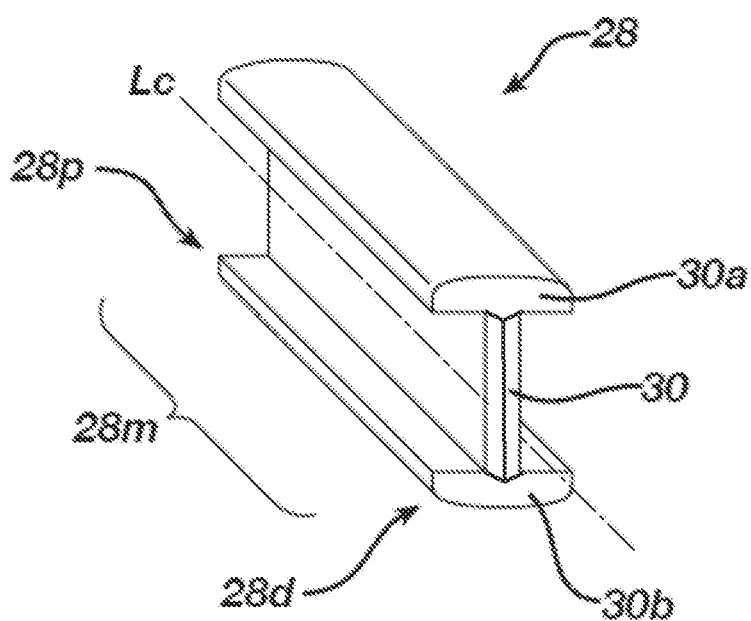
FIG. 3A is a perspective view illustration of one embodiment of a compression member including a cutting element.

The device can include a cutting element configured to transect tissue captured between the jaws, and the cutting element can be sized and shaped to transect or cut various thicknesses and types of tissue. In an exemplary embodiment, the cutting element can be positioned at the distal end 28d of the compression member 28, formed on the connecting portion 30c of the compression member 28. In some embodiments, such as the embodiment illustrated in FIG. 3, the cutting element can be integrally formed into the distal end 28d of the compression member 28. The cutting element can have a sharp or serrated edge configured to transect the tissue. In some embodiments, the cutting element can be recessed relative to distal ends of upper and lower flanges 30a, 30b of the I-beam compression member 28 so that compression occurs prior to transecting or cutting of the tissue. In another embodiment, the cutting element can be a knife blade that is not attached to a compression member such that the cutting element can advance and retract relative to the jaws without applying compression to the tissue. FIG. 3A illustrates one embodiment of the compression member 28 with a cutting element 30 as a sharp edge integrally formed into the distal end 28d of the compression member 28.

Referring back to FIG. 1, the surgical device 100 can have a closure actuator that can be configured to open and close the jaws 16a, 16b of the end effector 14. Manipulation of the closure actuator can pivot or otherwise move the jaws relative to one another such that the jaws can engage tissue, move anatomical structures, or perform other surgical functions. The closure actuator can have various sizes, shapes, and configurations, but in the illustrated embodiment the closure actuator includes the closure grip 20 and the stationary grip 22. The closure grip 20 can be moveable toward and away from stationary grip 22, such as via pivoting. In particular, the closure grip 20 can have a first position in which it is angularly offset from the stationary grip 22 and the jaws 16a, 16b of the end effector 14 are open. The closure grip 20 can have a second position where it is positioned adjacent to, or substantially in contact with, the stationary grip 22 and the jaws 16a, 16b of the end effector 14 can engage tissue and apply a force to tissue disposed therebetween. The closure grip 20 can be biased to the first open position with the jaws 16a, 16b of the end effector 14 being open, as shown in FIG. 1. The closure grip 20 can move the jaws 16a, 16b between the open and closed positions using manual or powered components. For example, in manually actuated embodiments, the closure grip 20 can be coupled to a gear that interacts with a rack disposed within the handle. Manual movement of the closure grip 20 toward the stationary grip 22 can move the rack distally toward the end effector 14, causing a force to be exerted onto the jaws 16a, 16b to close the jaws 16a, 16b. In powered embodiments, a motor can be disposed in the proximal handle portion 10 and manual movement of the closure grip 20 can cause a control signal to be sent to the motor, which can cause the jaws 16a, 16b to close. The closure grip 20 can interact with one or more locking features (not shown) configured to lock the closure grip 20 relative to the stationary handle 22. For example, the locking feature can automatically engage when the closure grip 20 substantially contacts the stationary handle 22 or the locking feature can automatically engage at each position the closure grip 20 is pivoted through, such as via ratcheting.

In certain embodiments the surgical device can also have a second actuator, such as the actuator 24, that can be separate from the closure actuator. The second actuator can be configured to advance a cutting element, apply energy to tissue, or both, and is referred to herein as a "firing actuator." The firing actuator 24 can have various sizes, shapes, and configurations, but in the illustrated embodiment can include a button or switch that can be depressed by a user. In another embodiment, the firing actuator 24 can include a trigger, switch, etc. that can be pivoted or otherwise moved by a user. Depressing or pivoting the actuator can activate various elements in the device, and can cause the cutting member to advance toward the end effector and/or cause energy to be delivered to the jaws. For example, depressing or pivoting the firing actuator can cause the compression member and/or the cutting member to advance distally and/or retract proximally relative to the jaws 16a, 16b. More specifically, the firing actuator can be in electrical communication with a motor disposed in the proximal handle portion 10. The motor can be operatively coupled to the compression member 28 using known components, such as a gear and rack. In this embodiment, activation of the motor can thus advance and/or retract the compression member 28.

Dynamic Motor Control

To address the shortcomings of controlling powered surgical devices described above, the devices and methods described herein can include a motor control mechanism that provides improved control over a motor powering the device. Improved control can be accomplished by dynamically changing an amount of power output from a motor in response to a manual user input. This can establish a direct correlation between, for example, the amount of pressure applied by a user to the firing actuator 24 and an amount of power output from the motor. In certain embodiments, the improved control can be implemented so as to provide a direct correlation between, for example, a position of a cutting element and a position of the firing actuator.

There are a number of ways in which such a correlation can be established. In one embodiment, a relationship between a reference signal (e.g., an electrical signal such as a voltage or resistance value) related a position of the firing actuator 24 can be compared to a position of a motor (e.g., as measured by an encoder coupled to the motor). Such a relationship can provide proportional position control of the jaws 16a, 16b or the cutting element 30c by detecting when a position of the firing actuator 24 is out of sync with a position of the motor. If the signals are out of sync, motor output power can be adjusted to bring the two signals into conformance with the expected relationship.

Figure 4:
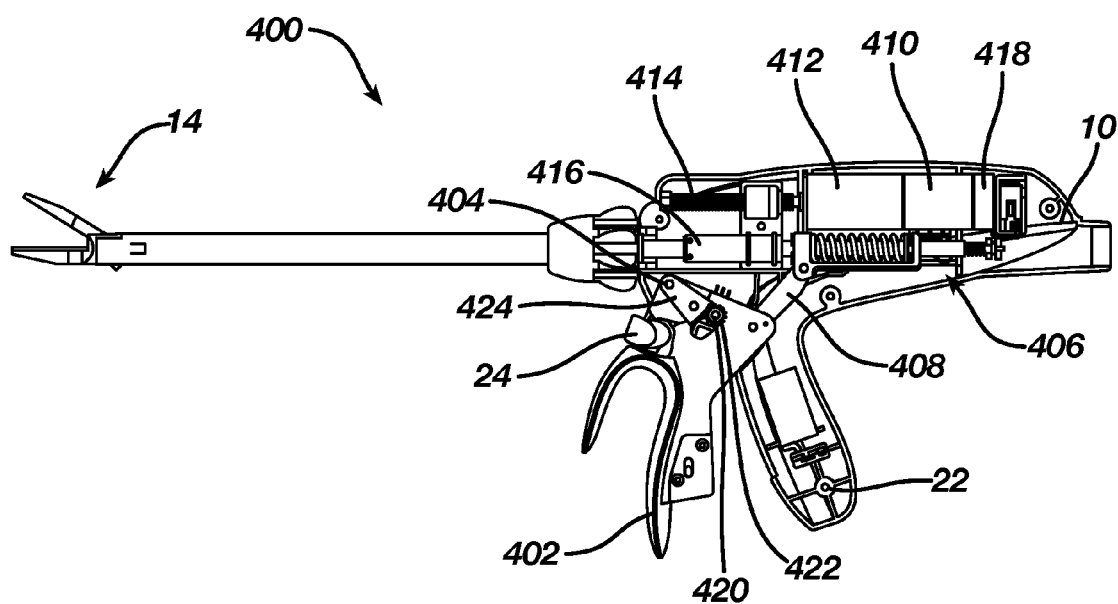
FIG. 4 is a cutaway side view illustration of a surgical device including one embodiment of a motor control mechanism.

FIG. 4 illustrates one embodiment of a surgical device 400 that includes this type of motor control mechanism. The device 400 can be similar to the device 100 described above and can include a handle portion 10, an end effector 14, a closure grip 402, and a stationary grip 22. The closure grip 402 shown in FIG. 4 can be pivotably coupled to the stationary grip 22 by pin 404. The closure grip 402 can also be coupled to a jaw closing mechanism 406 via a linkage 408. As a result, when a user pivots the closure grip 402 toward the stationary grip 22, the linkage 408 can actuate the jaw closure mechanism 406 to move the jaws of the end effector 14 from an open position (as shown in FIG. 4) to a closed position. Any of a variety of known jaw closure mechanisms can be employed, including, for example, direct motion drives. In other embodiments, a jaw closure mechanism can be configured to close the jaws to a given force using, e.g., a spring like that shown in the jaw closure mechanism 406.

Also visible in FIG. 4 is the motor 410, gear box 412, and drive screw 414. The drive screw 414 can be coupled to an outer shaft 416 such that rotational motion of the drive screw 414 is converted into translational movement of the outer shaft 416. The outer shaft 416 can be coupled to the compression member 28 in the end effector 14 such that translational movement of the outer shaft results in corresponding translational movement of the compression member. The motor 410 can therefore provide a driving force to actuate the compression member 28 and advance the cutting element disposed at the distal end 28d of the compression member through tissue engaged by the end effector 14.

Activation of the motor 410 can be controlled by the firing actuator 24 that is coupled to the closure grip 402. In typical operation, a user first draws the closure grip 402 into contact with the stationary grip 22 to close the jaws of the end effector 14 over tissue. After the end effector 14 is securely engaged to the tissue, the firing actuator 24 can be depressed by the user to drive the compression member 28 distally through the tissue. In some embodiments, the firing actuator 24 can also control the delivery of RF electrical or other energy into the tissue engaged by the end effector 14 to seal the cut being made by the cutting element disposed on the compression member 28. It should also be noted that, in certain embodiments, the firing actuator 24 can be prevented from actuating before the closure grip 402 is drawn toward the stationary grip 22 to close the jaws of the end effector.

The illustrated device 400 can also include components to form a motor control mechanism that provides proportional position control of, e.g., the compression member 28 relative to the firing actuator 24. For example, the motor 410 can be coupled to an encoder 418 such that a number of rotations of the motor can be counted. An exemplary encoder can include an emitter/detector pair and a striped target on the motor to detect rotation of the motor, as described in more detail below. The number of rotations of the motor 418 can be combined with a known gear ratio of the gear box 412 and thread pitch of the drive screw 414 to calculate a position of the compression member 28.

To detect a position of the firing actuator 24, a trigger assembly of the device 400 can include a potentiometer 420 coupled to the handle portion 10 and having a gear 422 coupled thereto. The gear 422 can engage a trigger linkage 424 that is coupled to the firing actuator 24. In particular, the firing actuator 24 and the trigger linkage 424 can be fixedly coupled to one another and configured to pivot together around pin 404. Accordingly, as a user depresses the firing actuator 24, the gear 422 of the potentiometer 420 can be rotated by the trigger linkage 424 and the output signal (i.e., voltage) of the potentiometer can change. A range of voltage values output from the potentiometer 420 can be correlated to the position of the firing actuator 24, and this range of values can also be correlated to a corresponding position of the compression member 28 (which can be determined using output from the encoder 418). For example, a voltage value of the potentiometer 420 when the firing actuator 24 is fully released can correspond to a proximal-most position of the compression member 28, and a voltage value of the potentiometer 420 when the firing actuator 24 is fully depressed can correspond to a distal-most position of the compression member 28. Using this information, control logic can impose a direct correlation between a position of the firing actuator 24 and a position of the compression member 28, such that the compression member is advanced distally as the firing actuator is depressed and the compression member is retracted proximally as the firing actuator is released.

Figure 5:
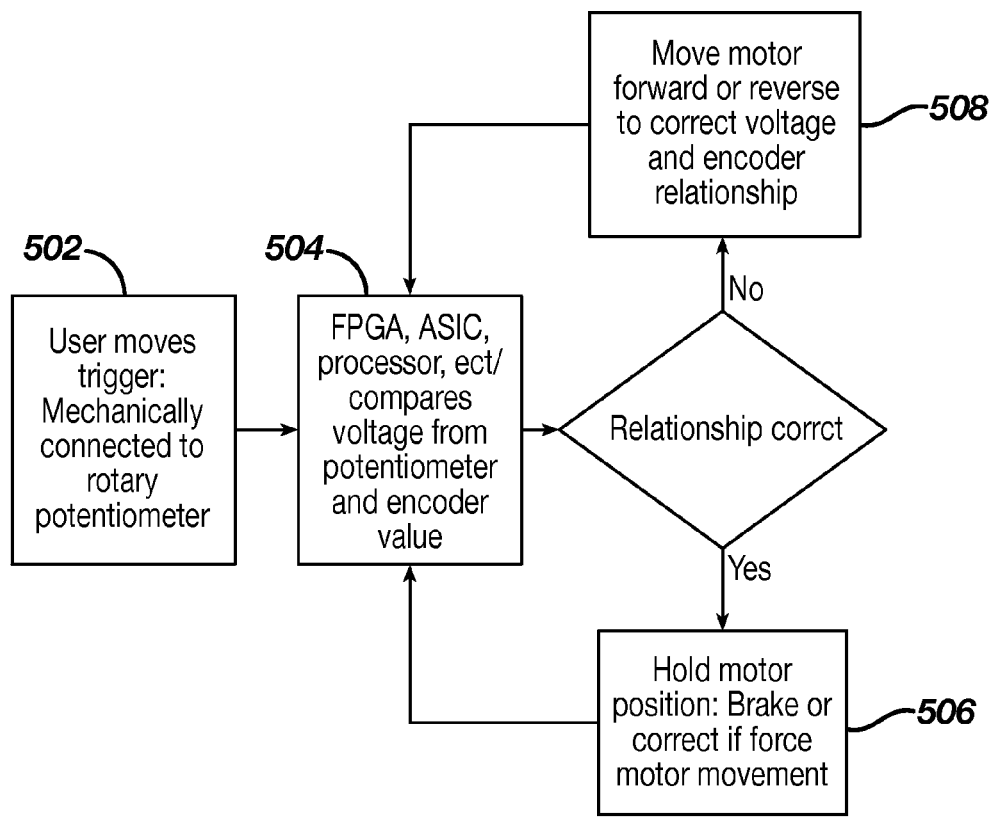
FIG. 5 is a flow chart of one embodiment of a dynamic motor control scheme for the device of FIG. 4.
Figure 6A:
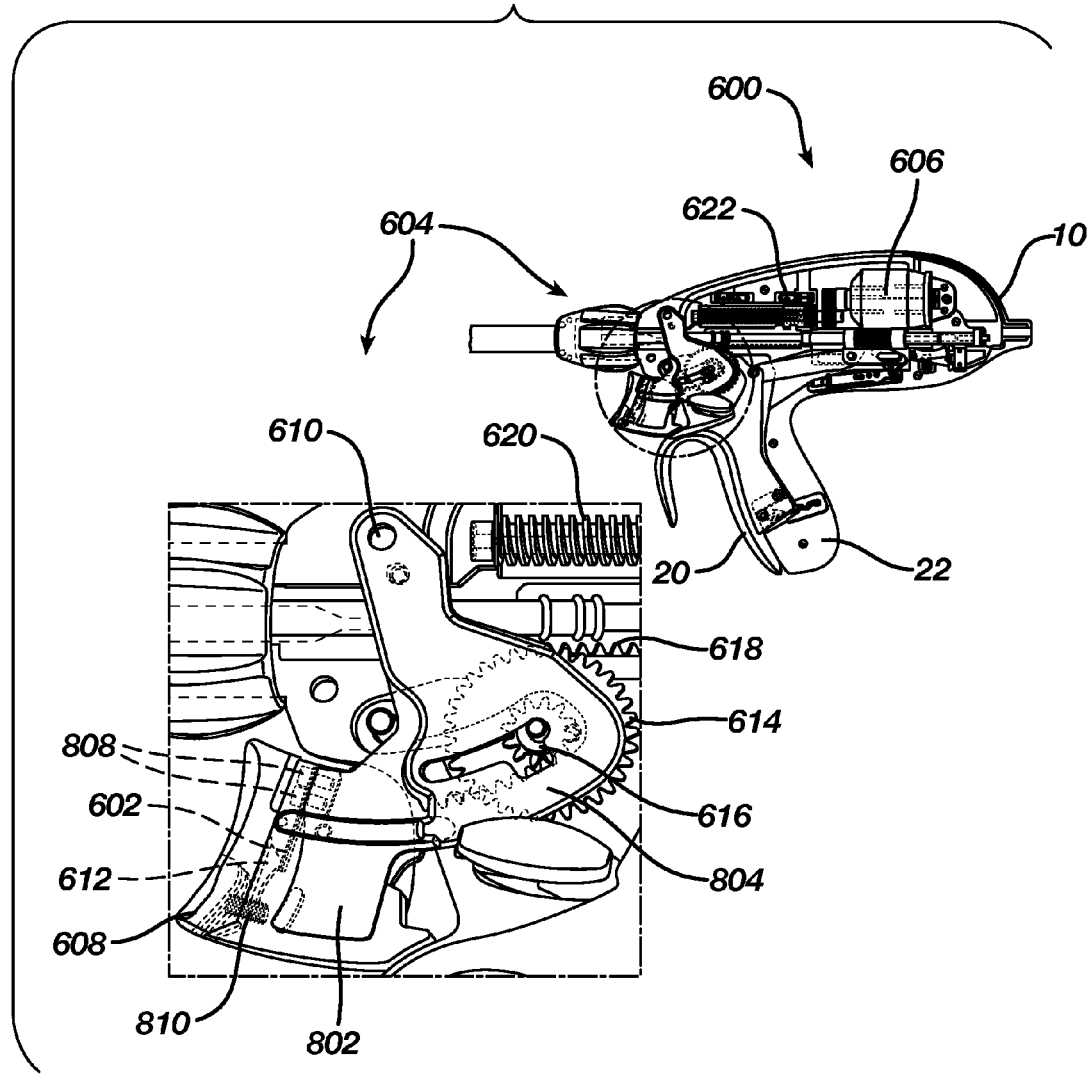
FIG. 6A is a cutaway side view illustration of an alternative embodiment of a surgical device including a motor control mechanism.
Figure 6B:
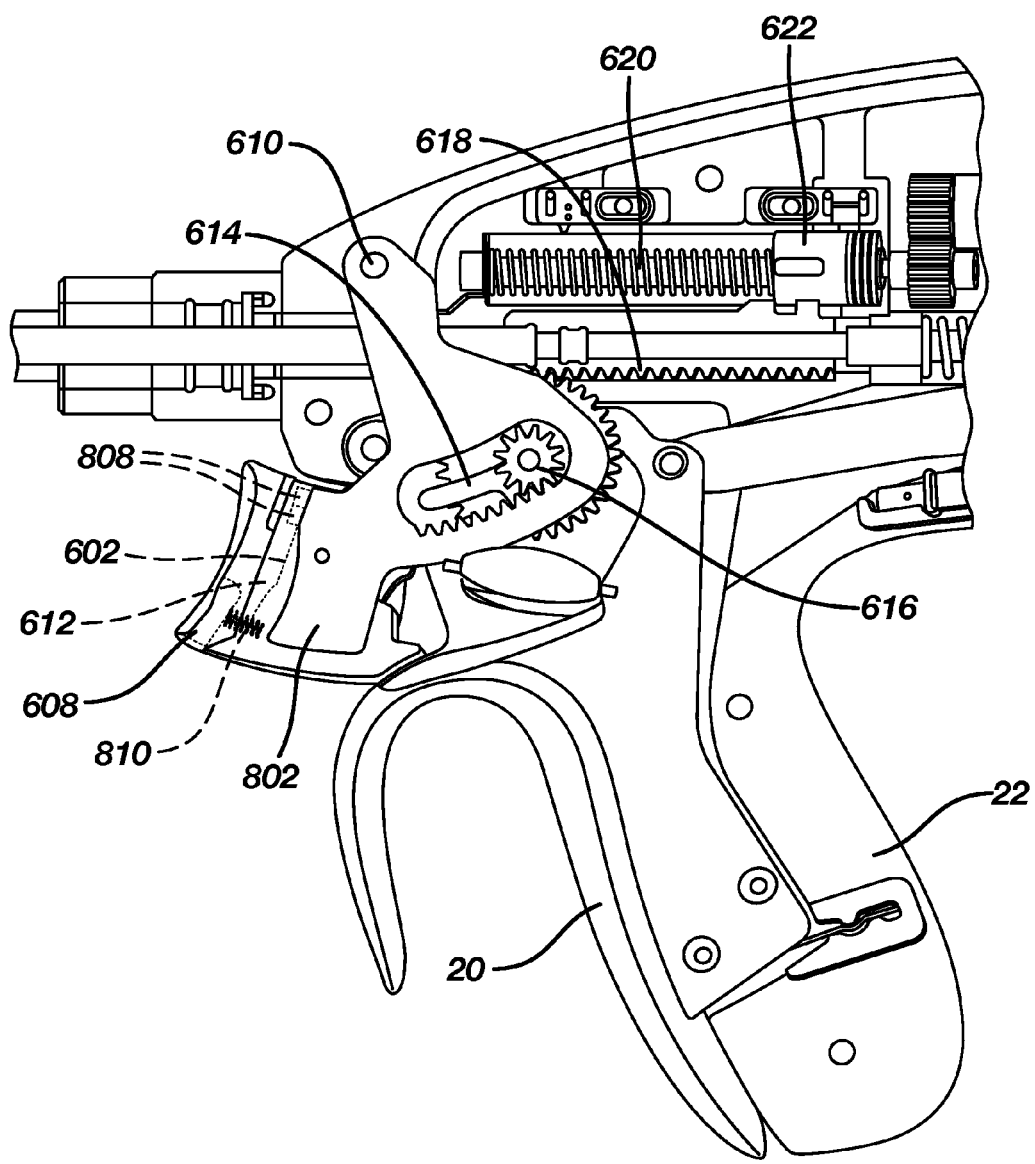
FIG. 6B is a detail view of the surgical device of FIG. 6A.
Figure 6C:
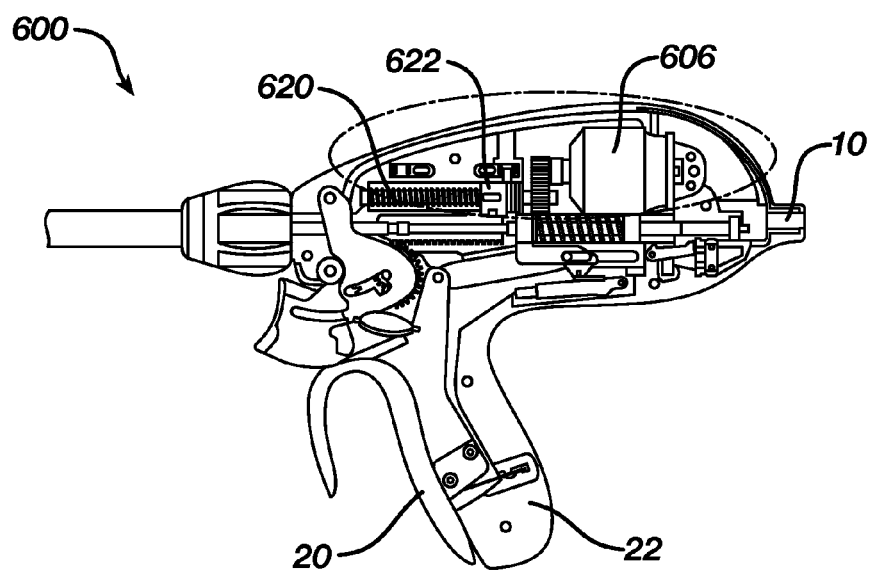
FIG. 6C is an alternative view of the surgical device of FIG. 6A.
Figure 6D:
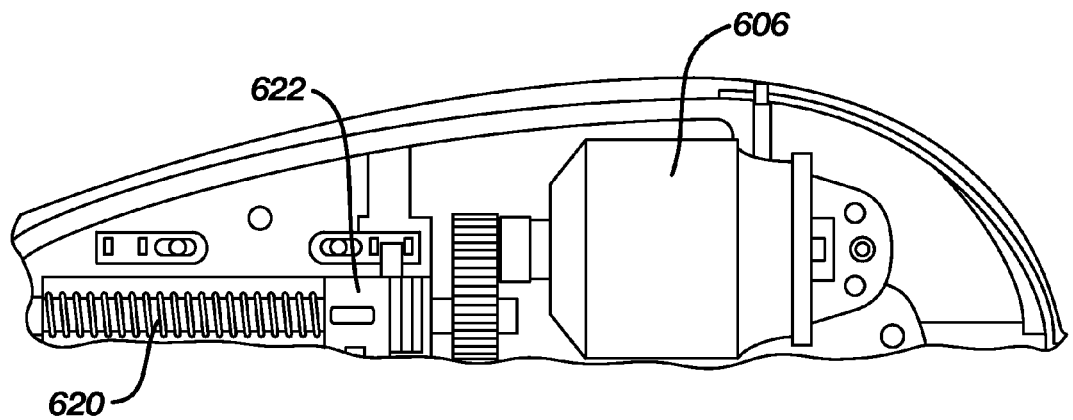
FIG. 6D is an alternative detail view of the surgical device of FIG. 6A.

FIG. 5 illustrates one embodiment of a method for implementing dynamic control of a motor power output in the device 400. As a user depresses or otherwise moves the firing actuator 24, the potentiometer 420 can be rotated and its output voltage adjusted, as shown in step 502. A processor (not shown), such as a field-programmable gate array (FPGA), application-specific integrated circuit (ASIC), or other data processor (analog or digital), can read the voltage output by the potentiometer and the value of the encoder 418 to determine both the position of the motor (and the compression member 28) and the position of the firing actuator or trigger 24, as shown in step 504. The two positions can be compared to an expected relationship (e.g., a stored reference value or other expression of the correlation described above) to determine if the compression member 28 is in sync with the position of the firing actuator 24. If the expected relationship is true, the motor can continue to be run at its current output power, as shown in step 506. Note that this can include holding the motor in a stationary position, as would be the case if the firing actuator 24 is not moving (e.g., a user is holding the firing actuator in a partially-depressed position). If the expected relationship is not true, as shown in step 508, output power of the motor can be increased or decreased, or the motor can be reversed if necessary, to bring the relationship between the position of the compression member 28 and the position of the firing actuator 24 into conformance with the expected relationship.

Accordingly, the device 400 can provide proportional position control of the cutting element in the end effector 14 based on the position of the firing actuator 24. This control is provided by correlating an output from an encoder 418 to an analog signal (e.g., a voltage) output from a potentiometer 420 coupled to the firing actuator 24. One of skill in the art will appreciate that there are a number of other configurations that could be used to correlate the position of the firing actuator 24 and the cutting element or compression member 28, certain of which are described below and all of which are considered within the scope of the present invention. In addition, while the embodiment described above uses the motor control mechanism to correlate a position of the firing actuator 24 and the compression member 28 having a cutting element disposed thereon, in other embodiments a similar configuration of components can be utilized to control other components of the device, e.g., motorized closing of the jaws of the end effector.

Tactile Feedback to User

In some embodiments, the devices and methods described herein can be configured to provide tactile or haptic feedback to a user through a trigger or other actuator, such as the firing actuator 24 described above. For example, advancing a cutting element (e.g., a cutting element disposed on a compression member 28, as described above) through tissue can require varying amounts of output power from a motor. The variation in required output power can be a function of tissue thickness, tissue composition, and any number of other factors. Accordingly, in certain embodiments, devices and methods described herein can be configured to communicate the varying levels of required power to a user as a form of haptic feedback. In such an embodiment, for example, a user would have to exert a greater force on a firing actuator to advance a cutting element through thicker or tougher tissue.

Providing haptic feedback can be accomplished in a variety of manners. In the embodiment illustrated in FIGS. 6A-6D, for example, a device 600 is shown that utilizes a strain gauge 602 integrated into a trigger assembly 604 (shown in the detail portion of FIG. 6) of the device. The strain gauge 602 forms an analog sensor that can be used to control the output power of a motor 606 that drives, for example, a cutting element disposed on an end effector at a distal end of the device, similar to the drive mechanisms described above. The output power of the motor 606 can be proportional to the force applied to a trigger 608, as measured by deflection of the strain gauge 602.

Figure 7:
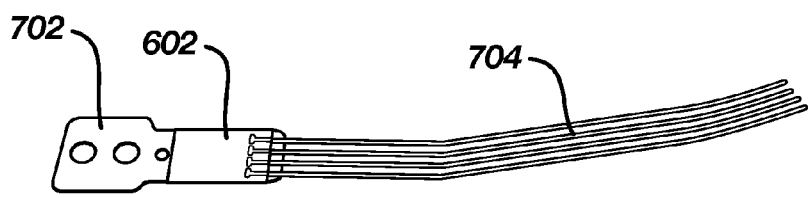
FIG. 7 is a depiction of one embodiment of the motor control mechanism of the device of FIG. 6.

FIG. 7 illustrates one embodiment of the strain gauge 602 in greater detail. The strain gauge 602 can be bonded to a leaf spring 702 such that the gauge can measure deflection of the leaf spring. Electrical leads 704 can extend from the strain gauge 602 to allow coupling to a digital data processor or other controller that can modulate output power of the motor 606 based on an electrical signal (e.g., a voltage) output from the strain gauge 602 and measured via the electrical leads 704.

Figure 8:
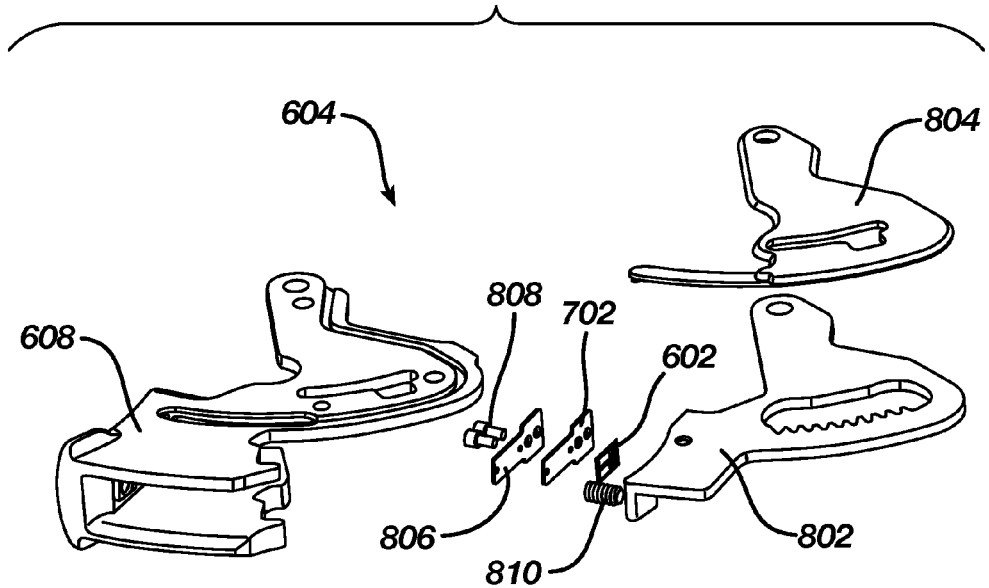
FIG. 8 is an illustration of the trigger assembly of the device of FIG. 6.

FIG. 8 illustrates an exploded view of the trigger assembly 604 shown in FIGS. 6A-6D. The assembly can include the trigger 608, a linkage 802, and a guide member 804. The assembly 604 can also include a leaf spring 610, as well as a second leaf spring 806 in some embodiments. The strain gauge 602 can be bonded to the leaf spring 610 and the leaf spring (or springs) can be coupled to the linkage 802 via mounting bolts 808. Also shown is a rod 810 that can be threadably coupled to the trigger 608 to serve as a rigid stop to prevent excessive deformation of the leaf spring 610.

Referring back to FIGS. 6A-6D, the trigger assembly 604 can be explained in more detail. In particular, the trigger 608, linkage 802, and guide member 804 can be pivotably coupled to a handle portion 10 of the device 600 by a pin 610. Further, at least the trigger 608 and the linkage 802 can be configured to pivot independently of one another about the pin 610. At a distal-most end of the linkage 802, the strain gauge 602 and leaf springs 702, 806 can be coupled to the linkage via the mounting bolts 808, though other known methods for mechanical coupling can be employed, including, e.g., glue or other adhesives, snap or friction fit components, or complementary tabs and slots formed on the various components. Note that the mounting bolts 808 (or other mechanical coupling) are located at one end of the leaf springs 702, 806 such that the strain gauge 602 is bonded to a portion of the leaf spring 702 that is cantilevered in space from the linkage 802. Finally, a proximal-facing inner surface of a distal end of the trigger 608 can include a protrusion 612 formed thereon that can abut against the leaf spring 806 on an opposite side from the strain gauge 602.

Also shown in FIGS. 6A-6D are two coupled gears 614, 616 that can couple the linkage 802 to a rack 618 that can in turn be coupled to a cutting element (not shown) of the device. The rack 618 can also be coupled to a drive screw 620 by a follower 622 that translates along the drive screw 620 as the drive screw rotates, similar to the operation of the device 400 described above.

In operation, a user can first draw a closure grip 20 of the device 600 toward a stationary grip 22 into the configuration shown in FIGS. 6A-6D, thereby closing opposed jaws of an end effector (not shown) to engage tissue. A user can then depress the trigger 608 to begin advancing a compression member and cutting element (not shown) through the tissue engaged by the jaws. As the user depresses the trigger 608, the protrusion 612 can deflect the leaf springs 702, 806 toward the linkage 802, thereby causing a change in an electrical signal output from the strain gauge 602 (e.g., an increase in voltage or measured resistance, etc.). This change can be monitored by a digital data processor or other circuit element and can be used as a signal to activate the motor 606.

If the activation power of the motor 606 is sufficient to overcome the force required to advance a cutting element through tissue, the follower 622 will move distally along the drive screw, carrying the rack 618 with it. Distal movement of the rack 618 can cause rotation of the coupled gears 614, 616, that can in turn cause the linkage 802 to retract proximally. If the user does not depress the trigger 608 further, the proximal movement of the linkage 802 will reverse the deflection of the leaf springs 702, 806, and the motor 606 will stop. On the other hand, if the user continues to depress the trigger 608 at a steady rate, the deflection of the leaf springs 702, 806 will remain constant along with the output of the motor 606.

If, however, a variation in the force required to advance a cutting element through tissue is encountered, e.g., due to a variation in tissue thickness or toughness, an operating power of the motor 606 may not be sufficient and the cutting element will slow or stop advancing. This can cause the linkage 802 to stop retracting proximally and deliver feedback to the user in the form of increased resistance from the leaf springs 702, 806 as the user attempts to depress the trigger 608 further. If the user applies increased pressure to depress the trigger 608 further, the increased deflection of the leaf springs 702, 806 can cause a change in an electrical signal output from the strain gauge. This change in the electrical signal output from the strain gauge can cause a controller to increase the output power of the motor 606. When the increased output power reaches a level sufficient to advance the cutting element (and rack 618 coupled thereto), the linkage 802 will again retract as described above.

As a result, the device 600 can provide an intuitive control mechanism for dynamically changing the output power of a motor. The user interactions with the device can closely approximate those of a manually-operated instrument, but without requiring the user to apply large magnitude forces to the device. Furthermore, the mechanical configuration of the trigger assembly components can provide force feedback to a user regarding the toughness of tissue encountered in the cutting operation, increasing a user's situational awareness. This can allow a user to experience the same level of feedback and intuitive control found in manually-operated devices while providing the advantages of motor assistance.

Figure 9A:
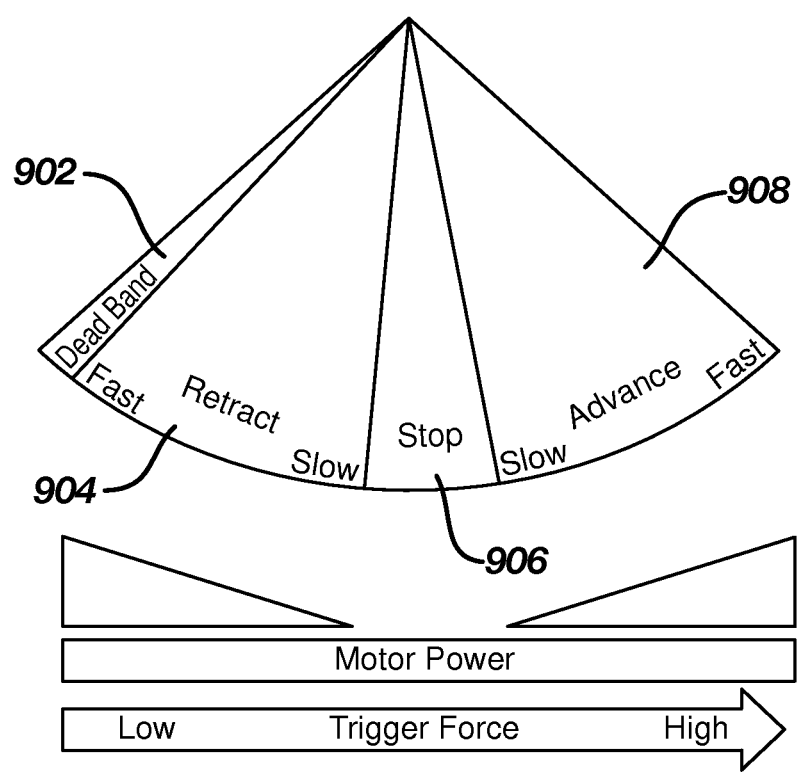
FIG. 9A is an illustration of one embodiment of a correlation between trigger movement and motor power.
Figure 9B:
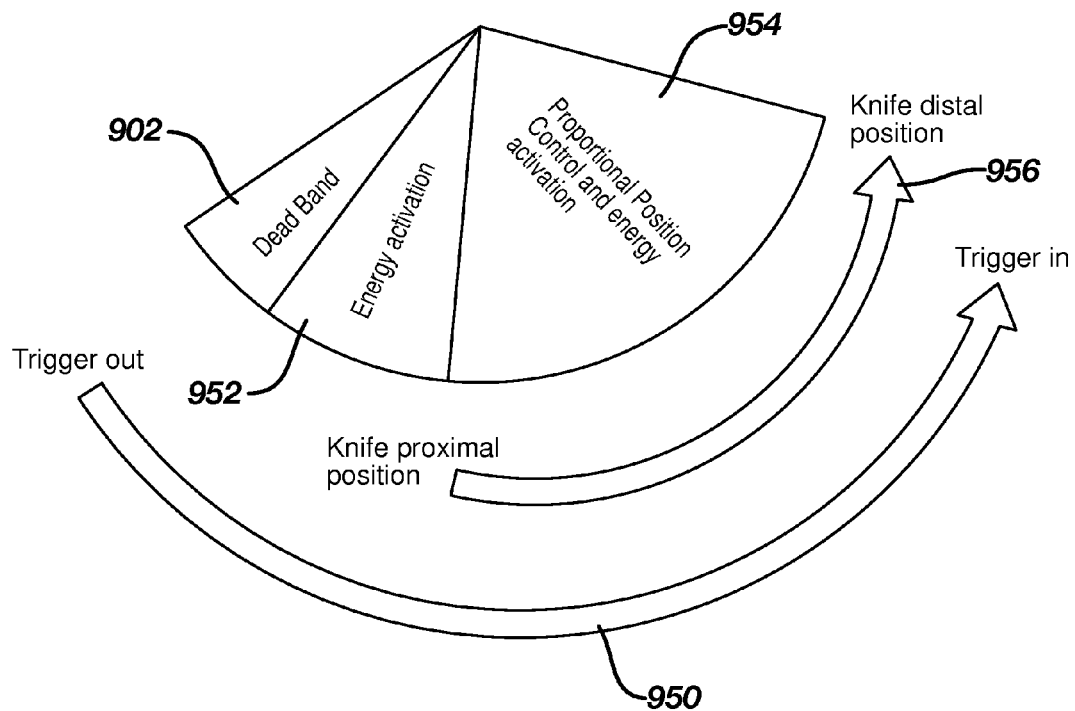
FIG. 9B is an illustration of one embodiment of a correlation between trigger movement, motor power, and energy delivery to tissue.

FIGS. 9A and 9B graphically illustrate embodiments of how an analog signal from the strain gauge 602 can be subdivided to provide intuitive control of a motorized cutting element and/or compression member. In particular, the figures depict how the electrical signal, e.g., from the strain gauge 602, can be simultaneously mapped to both logic and variable speed control of the motor 606 for both advancing and retracting a cutting element and/or compression member, as well as triggering delivery of energy to seal tissue being transected. As shown in each figure, the left edge of the arc can define a dead band or zone 902 to provide some tolerance accommodating minor sensor drift from an initial null value during device operation. Application of additional force to the trigger 608 can cause increased deflection of the leaf springs 702, 806, resulting in a change in the electrical signal (e.g., increased voltage or measured resistance) output from the strain gauge 602. In a retraction band 904 shown in FIG. 9A adjacent to the dead zone 902, the electrical signal of the strain gauge 602 can be equated with variable speed (or, in some embodiments, a single speed regardless of position within the band) retraction of the cutting element and/or compression member. A proximally-located electrical limit switch can be employed to stop the motor 606 from attempting to further retract the cutting element and/or compression member once the switch closes (e.g., once the cutting element is fully retracted).

Further application of force to the trigger 608 can enter the stop band 906 of FIG. 9A where the motor 606 is halted to stop retraction or advancement progress. This can occur at any point along the cutting element stroke length (e.g., half-way between a proximal and distal end of the cutting element path through the end effector). The stop band 906 can span a particular range of sensor output wide enough to prevent operator-induced oscillation of the cutting element.

Still further application of force to the trigger 608 can enter the advancement band 908 of FIG. 9A where the electrical signal of the strain gauge 602 is equated with variable speed (or, in some embodiments, a single speed regardless of position within the band) advancement of the cutting element and/or compression member. Similar to the retraction band 904 discussed above, a distally-located electrical limit switch can be employed to prevent the motor 606 from attempting to further advance the cutting element once the switch closes (e.g., once the cutting element is fully advanced). Accordingly, in certain embodiments when the cutting element is in a fully retracted position, the retraction band 904 and stop band 906 can be inactive, and advancement will not begin until a user depresses the trigger 608 far enough to enter the advancement band 908. Once this occurs and the cutting element is advanced distally, the stop band 906 and retraction band 904 can become active. Similarly, when the cutting element is fully advanced distally, the stop band 906 and advancement band 908 can be inactive, and retraction will not begin until a user releases the trigger enough to enter the retraction band 904. Once this occurs and the cutting element is retracted proximally, the stop band 906 and advancement band 908 can become active. In other embodiments, the stop band 906 can always be active (as its effect is always to halt motion of the cutting element) and solely the retraction band 904 or advancement band 908 can be deactivated based on the above-described positions of the cutting element.

FIG. 9B provides an alternative illustration of control logic for mapping trigger position to cutting element (or closure jaw) position, as well as application of energy to tissue being transected. For example, application of force to the trigger 608 to move the trigger from its outward-most position (as shown by the trigger position arc 950) can enter an energy activation band 952 wherein RF or other energy is delivered into the tissue captured between the jaws. In some embodiments, while the trigger is in the energy activation band 952, the cutting element can remain stationary at a proximal position.

As a user continues to depress the trigger 608, the trigger position can enter a position control band 954, wherein proportional position control of the cutting element can be implemented as described above, in combination with delivery of RF or other energy into the tissue being transected by the cutting element. Accordingly, while the trigger 608 is being moved through the position control band 954, the cutting element can be advanced or retracted along the length of the jaws as shown by the knife position arc 956. Any of the proportional position control schemes discussed above can be utilized to control the position of the cutting element when the trigger is being passed through the band 954.

Motor Braking for Improved Cutting Element Control

Another problem of prior art motorized devices is a lack of precision in controlling movement of a cutting element and/or compression member, especially in a case where a user stops providing a manual input that activates the motor. An example may be a situation where a user suddenly releases a firing actuator or trigger upon realizing that a cutting element has been advanced too far. In a manually-operated device, the user's release of an actuation member would immediately stop movement of the cutting element. In a motorized device, however, the kinetic energy of the motor's rotating components has to be dissipated before the cutting element will stop advancing.

The devices and methods described herein can address this problem by immediately stopping a motor from supplying an output power when a manual user input ceases. In one embodiment, this can be accomplished by providing a device, such as the device 600 described above, with a motor brake that can quickly dissipate energy stored in the motor. There are a number of motor brakes known in the art, including mechanical and electrical mechanisms. While any known motor braking mechanism can be utilized, it can be advantageous in certain embodiments to utilize an electrical braking mechanism because there is no need to include additional heavy components in the device for the purpose of braking the motor.

Figure 10:
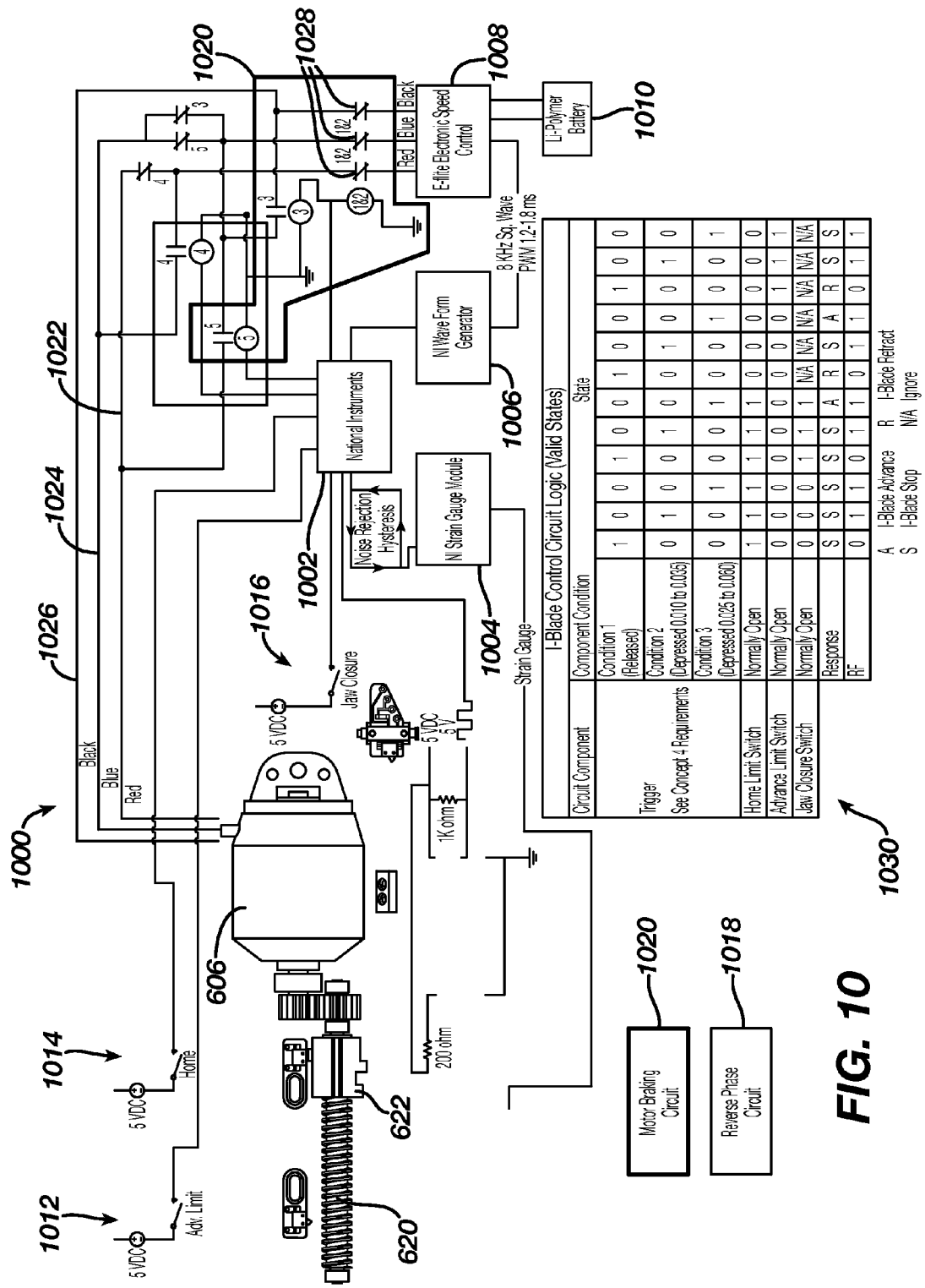
FIG. 10 is a schematic illustration of one embodiment of a circuit design for a surgical device including a motor control mechanism.

FIG. 10 illustrates one embodiment of a control circuit 1000 for the surgical device 600 described above. The control circuit 1000 includes the three-phase alternating current (AC) motor 606, a digital data processor 1002, a strain gauge controller 1004, a waveform generator 1006, a three-phase motor controller 1008, and a battery 1010. Also shown are a variety of electrical limit switches 1012, 1014, 1016 that are used to indicate complete advancement of the a cutting element, complete retraction of a cutting element, and closure of the opposed jaws of an end effector, respectively.

The control circuit 1000 further includes a number of standard circuit elements (e.g., resistors, capacitors, inductors, switches, etc.) arranged to provide, for example, a reverse phase circuit 1018 that reverses a rotation direction of the motor 606, and a motor braking circuit 1020 that quickly halts rotation of the motor. The motor braking circuit 1020 works by disconnecting the three electrical leads 1022, 1024, 1026 of the motor 606 from the battery 1010 and coupling the leads together using switches 1028. Connecting the leads together and isolating the circuit from the battery 1010 can allow the motor 606 to generate current that can be dissipated internally, thereby reducing the amount of energy that is dissipated kinetically by further rotation of the motor 606.

The motor braking circuit 1020 has a number of advantages over other braking mechanisms. For example, the motor braking circuit 1020 requires no heavy braking mechanisms be added to the device, as the motor itself is used as the braking mechanism. Further, higher motor speeds result in greater braking torque with the illustrated motor braking circuit, which means braking efficiency scales with increased demand. Despite these advantages, however, one of skill in the art will appreciate that a number of other motor braking circuits and/or mechanisms can be used. These can include, for example, connecting the electrical leads 1022, 1024, 1026 to a resistive load, applying reverse power polarity and monitoring motor speed with, e.g., an encoder, as well as any number of mechanical braking mechanisms. Regardless of which mechanism is employed, an output power of a motor can be immediately stopped in response to cessation of a manual user input, resulting in an immediate halt to the advancement or retraction of a cutting element.

FIG. 10 also illustrates one embodiment of a logic diagram 1030 for the control circuit 1000. The logic diagram 1030 details the state of a cutting element (e.g., advancing, retracting, stopped, etc.) and RF energy delivery given a number of different possible combinations of trigger position (e.g., released, partial depression to a threshold level, partial depression beyond the threshold level, etc.), cutting element position (e.g., full advancement to limit switch 1012, full retraction to limit switch 1014, etc.), and jaw position (e.g., closed, open, etc.). Detailed description of each illustrated state is omitted here but, in general, it can be seen that the cutting element is not advanced until the trigger is sufficiently depressed and the jaws are closed. Further, releasing the trigger after advancement has begun can retract the cutting element, while partially releasing the trigger can hold the cutting element in its current position (e.g., as shown in FIG. 9). Still further, regardless of where the trigger is, the cutting element will not be advanced further once it reaches the distally-positioned limit switch 1012. Of course, other embodiments of the logic diagram 1030 are also possible and may implement different behaviors for the device.

Multi-Stage Trigger Mechanisms

In some embodiments, it can be desirable to implement delivery of RF energy before beginning to advance a cutting element through tissue. For example, delivering RF energy to tissue engaged by jaws of an end effector can begin to desiccate the tissue, which reduces its thickness and the force required to pass a cutting element therethrough. As mentioned above, however, including multiple controls on a device can become taxing for a user. Accordingly, in certain embodiments, a multi-stage trigger mechanism can be employed to provide for sequential activation of RF energy delivery and cutting element and/or compression member advancement.

Figure 11A:
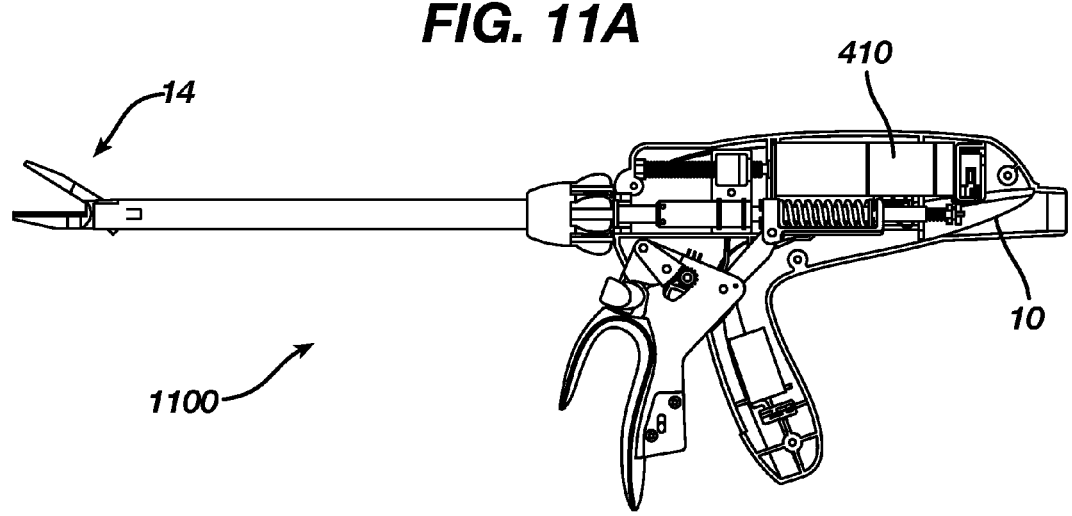
FIG. 11A is a cutaway side view illustration of an alternative embodiment of a surgical device including a motor control mechanism.
Figure 11B:
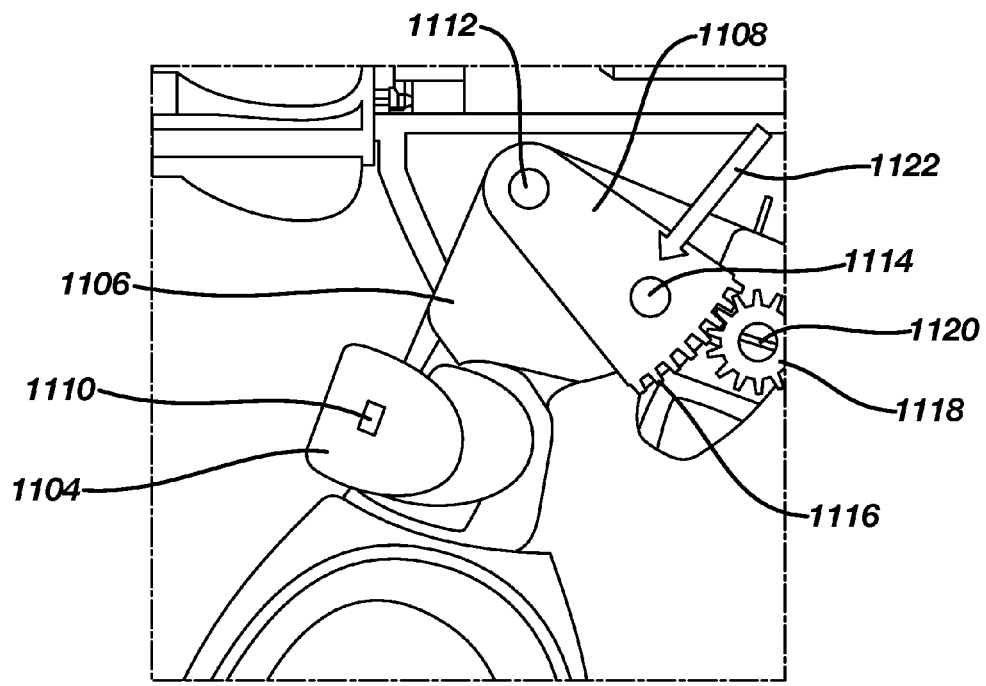
FIG. 11B is a detail view of the trigger assembly shown in FIG. 11A.

FIGS. 11A and 11B illustrate one embodiment of a surgical device 1100 (similar to device 400 described above) having a multi-stage trigger assembly 1102 (shown in detail in FIG. 11B). The trigger assembly 1102 can include a trigger 1104, a first linkage 1106, and a second linkage 1108. The trigger 1102 can be slidably coupled to the first linkage 1104 such that the trigger 1102 can move proximally-distally relative to the first linkage 1104. Furthermore, a switch 1110 can be positioned on a surface of the first linkage 1104 such that proximal movement of the trigger 1102 depresses the switch 1110. In addition, the trigger 1102 can be biased in a proximal direction using a spring or other known biasing member such that the switch 1110 does not remain depressed when, e.g., a user releases the trigger 1102.

The first linkage 1106 and the second linkage 1108 can be pivotably coupled to a handle portion 10 of the device 1100 by a pin 1112. The first and second linkages 1106, 1108 can also be coupled to one another, e.g., using an interfacing protrusion 1114 formed on the first linkage 1106 and through-hole formed on the second linkage 1108, such that the two components pivot about pin 1112 together. Still further, a surface of the second linkage 1108 can include a toothed gear rack 1116 that interfaces with a gear 1118 that is coupled to a potentiometer 1120 (the potentiometer 1120 can be mounted to the handle portion 10 of the device 600 similar to the potentiometer 420 and trigger linkage 424 discussed above). The first and second linkages 1106, 1108 can also be biased toward a distal position (e.g., a trigger release position) by a spring, represented by arrow 1122.

As described above in connection with FIG. 4, an output signal (e.g., a voltage) from the potentiometer 1120 can be utilized to control a speed of a motor 410 disposed within the device 1100. In addition, the switch 1110 can be coupled to an RF controller such that depression of the switch triggers the delivery of RF power to tissue engaged by the end effector 14 of the device. As a result, the device 1100 can provide a two-stage trigger assembly for the sequential delivery of RF energy and motorized advancement of a cutting element. In particular, as a user begins to depress the trigger 1104, the bias of the spring 1122 can prevent proximal movement of the first and second linkages 1106, 1008. The trigger 1104 can therefore move proximally relative to the first linkage 1106 and depress the switch 1110, starting the delivery of RF energy. As the user continues to depress the trigger 1104 proximally, the biasing force of the spring 1122 can be overcome and the first and second linkages 1106, 1108 can begin pivoting proximally about pin 1112. The movement of the second linkage 1108 can rotate the gear 1118 and potentiometer 1120, thereby triggering a change in the amount of power output by the motor 410, as described above.

In another embodiment illustrated in FIGS. 12A-12F, a multi-stage trigger assembly is provided without the need for an additional switch 1110. In such an embodiment, an output from a single sensor can be utilized for multiple purposes, either sequentially or simultaneously. For example, in the illustrated embodiment, an output signal (e.g., voltage) range of a potentiometer can be divided into a plurality of portions, wherein a first portion can be configured to trigger delivery of RF energy and a second portion can be configured to trigger variable activation of a motor coupled to a cutting element. Further, a series of springs can be included that can be selectively engaged as the trigger is depressed. The varying levels of resistance provided by the springs can communicate feedback to a user regarding which stage is being activated. This configuration allows for control of multiple device functions using only a single sensor, thereby reducing costs and simplifying device design.

Figure 12A:
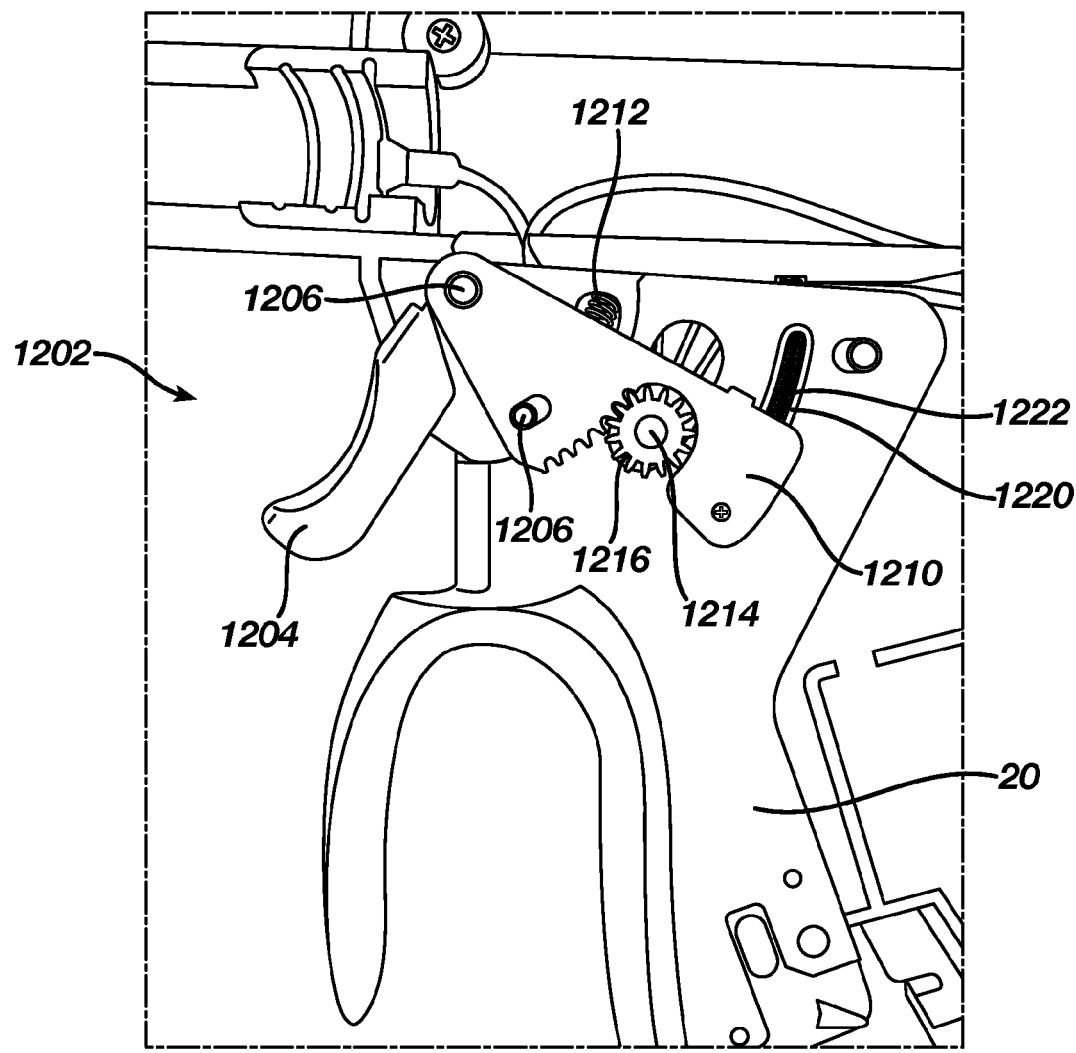
FIG. 12A is a depiction of an alternative embodiment of a trigger assembly of a surgical device including a motor control mechanism.
Figure 12B:
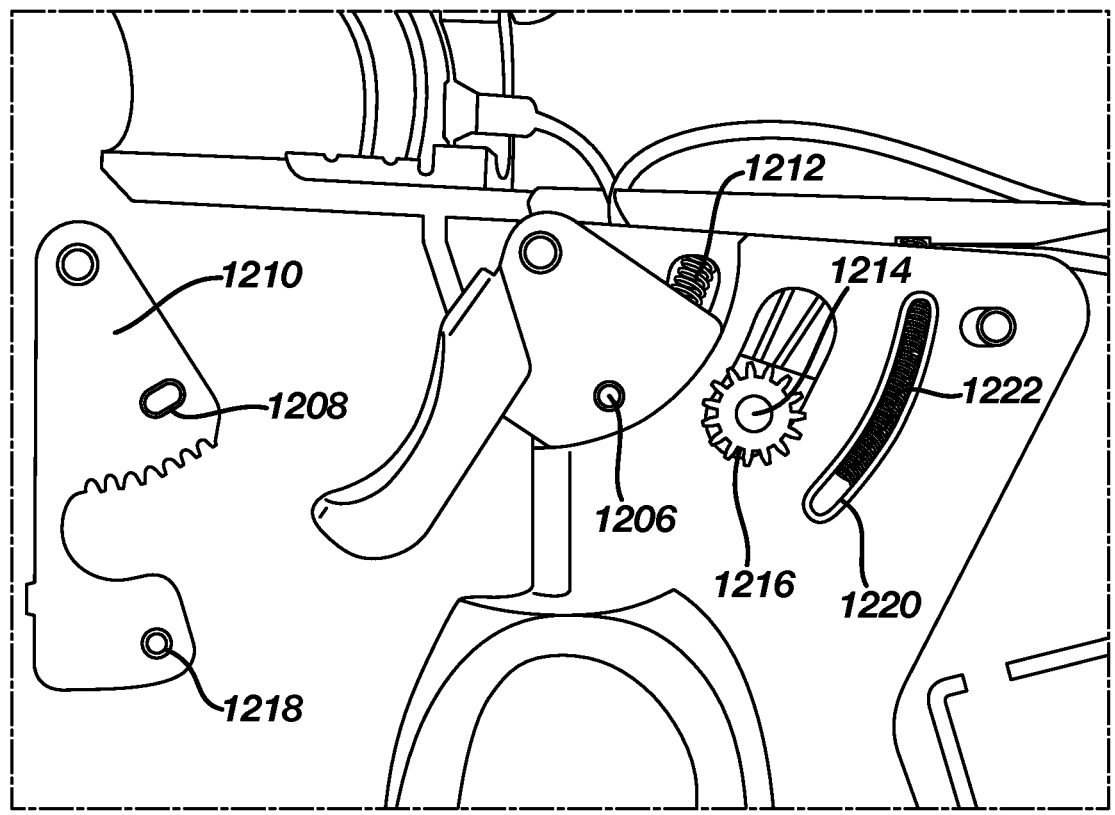
FIG. 12B is a depiction of the trigger assembly of FIG. 12A partially disassembled.

As shown in the assembled view of FIG. 12A and partially-exploded view of FIG. 12B, a trigger assembly 1202 can include a trigger 1204 pivotably coupled to a closure grip 20 via a pin 1206. The trigger 1204 can include a protrusion 1206 formed thereon that is configured to interface with a through-hole 1208 of a linkage 1210 such that the linkage 1210 and trigger 1204 pivot about the pin 1206 together through at least a portion of the trigger travel. In addition, a first spring 1212 can bias the trigger 1204 distally relative to the closure grip 20. Also shown is a potentiometer 1214 coupled to a gear 1216, and a toothed rack surface 1217 formed on the linkage 1210 that interfaces with the gear.

The linkage 1210 can include a protrusion 1218 formed thereon (shown in FIG. 12B) that extends through a slot 1220 formed in the closure grip 20 when assembled. A second spring 1222 positioned on an opposite side of the closure grip 20 can bias the protrusion 1218 toward a lower, distal end of the slot 1222. The second spring 1222, however, can be sized such that it does not exert a force (or does not exert a significant force) on the protrusion 1218 of the linkage 1210 until the protrusion reaches a predetermined point between the endpoints of the slot 1222.

Figure 12C:
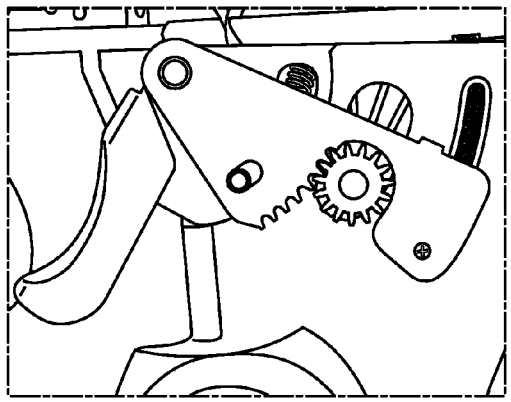
FIG. 12C is a depiction of the trigger assembly of FIG. 12A in a disengaged position.
Figure 12D:
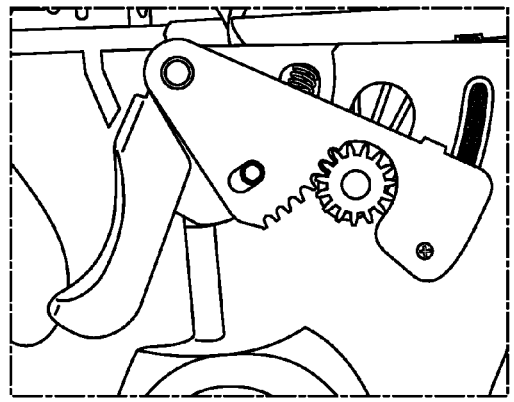
FIG. 12D is a depiction of the trigger assembly of FIG. 12A in a first partially engaged position.

Operation of the multi-stage trigger shown in FIGS. 12A-12B is illustrated in FIGS. 12C-12F. In FIG. 12C, the trigger 1204 is in a starting position, where it is fully released and biased proximally by the spring 1212. As a user begins to apply pressure to the trigger 1204, it will pivot around pin 1206 against the bias of the spring 1212, as shown in FIG. 12D. Note that the through-hole 1208 formed in the linkage 1210 has an oblong shape that provides for some degree of trigger depression before the linkage 1210 begins rotating the potentiometer 1214. This can provide a degree of safety to guard against inadvertent activation of the device. Once the protrusion 1206 on the trigger 1204 abuts against the end of the through-hole 1208, the linkage 1210 will begin pivoting with the trigger 1204, and the teeth of its rack 1217 will engage the gear 1216 to rotate the potentiometer 1214. The rotation of the potentiometer 1214 can cause an electrical signal output from the potentiometer to change, but to remain within a first range associated with the partial depression of the trigger shown in FIG. 12D. A controller coupled to the potentiometer can detect this change, determine that the signal value falls within the first range, and trigger the delivery of RF electrical energy into tissue engaged by an end effector of the device.

Figure 12E:
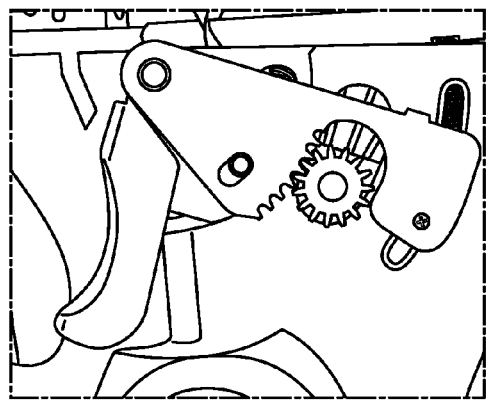
FIG. 12E is a depiction of the trigger assembly of FIG. 12A in a second partially engaged position.
Figure 12F:
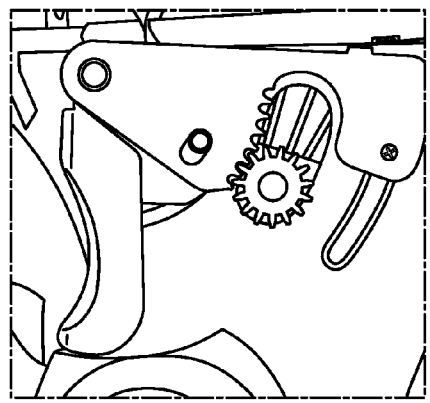
FIG. 12F is a depiction of the trigger assembly of FIG. 12A in a fully engaged position.

As the user continues to depress the trigger 1204, the protrusion 1218 extending from the linkage 1210 into the slot 1220 can come into contact with the second spring 1222, as shown in FIG. 12E. The increased resistance provided by the spring 1222 can communicate to the user that a second stage of device actuation has been initiated. Furthermore, the electrical signal output from the potentiometer can enter a second range that triggers activation of the motorized cutting element, as described above. For example, in some embodiments movement of the trigger in the second range can result in corresponding advancement or retraction of a cutting element via a motor and associated motor control mechanism such that a position of the trigger 1204 is proportional to a position of the cutting element. In this manner, the cutting element can continue to be advanced in accord with changes in the potentiometer signal output until the trigger is fully depressed, as shown in FIG. 12F.

Accordingly, a multi-stage trigger assembly is provided that eliminates the need for a separate switch, but continues to allow for controlled and sequential activation of RF energy and motorized cutting using a single control element. Such an embodiment effectively utilizes a single sensor output to control multiple device functions occurring in series or sequentially. For example, within the second range of potentiometer output RF energy can continue to be applied as within the first range, or can be applied under different parameters (e.g., power level), etc.

Figure 13:
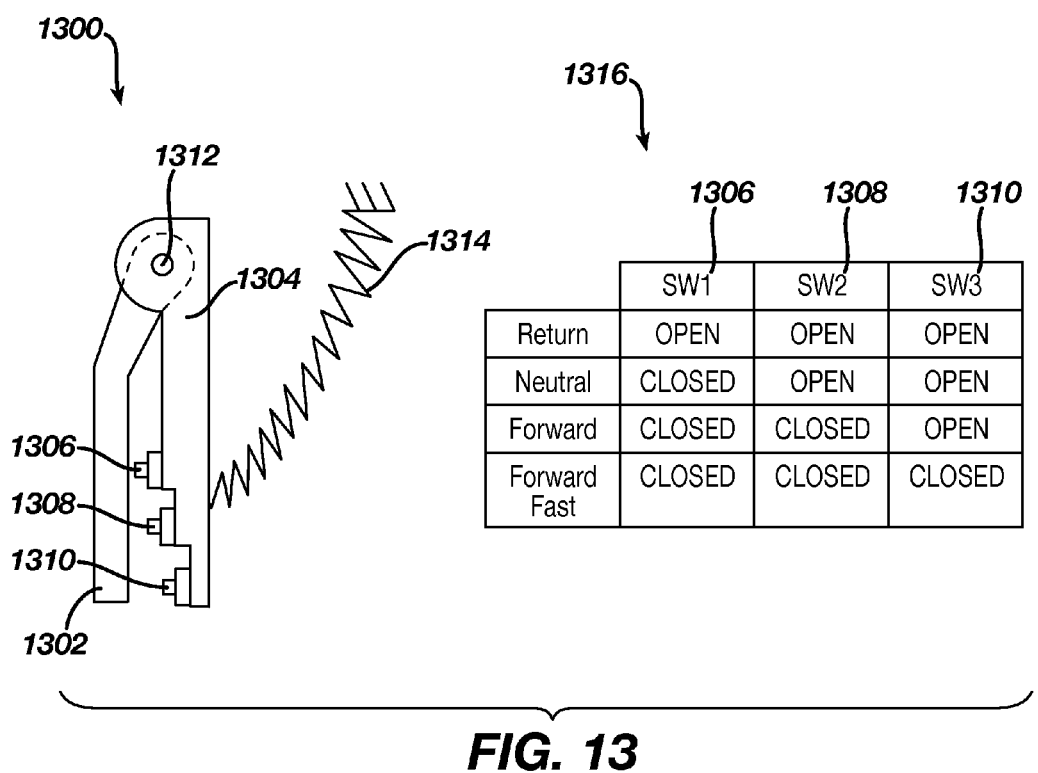
FIG. 13 is a side view illustration of an alternative embodiment of a trigger assembly of a surgical device including a motor control mechanism.

Still another variation on the multi-stage trigger assembly is illustrated in FIG. 13. In this embodiment, a trigger assembly 1300 is provided that includes a plurality of discrete switches arranged along a length of a trigger 1302 such that depressing the trigger sequentially activates each of the switches. In the illustrated embodiment, a linkage 1304 has mounted thereto a first switch 1306, second switch 1308, and third switch 1310. The linkage 1304 can have a stepped or curved surface such that the trigger 1302 sequentially contacts and actuates the first switch 1306, second switch 1308, and third switch 1310 as it is pivoted about pin 1312 toward the linkage 1304. The trigger 1302 and linkage 1304 can be pivotably mounted to a handle portion of a device and biased toward a released state by a spring 1314, or the linkage 1304 can be rigidly coupled to a device such that the trigger is the only component that pivots about the pin 1312.

Also shown in FIG. 13 is a logic diagram 1316 that illustrates the motorized action of a cutting element in response to the various states of the switches 1306, 1308, 1310. As can be seen in the diagram, releasing the trigger 1302 can result in retraction of the cutting element. Similarly, if the trigger is only slightly depressed (i.e., only the first switch 1306 is depressed), the position of the cutting element can be held, and the cutting element can be advanced at sequentially higher speeds as the second and third switches 1308, 1310 are depressed. One of skill in the art will appreciate that any number of switches can be used to provide additional control levels or additional features. For example, an additional switch can be included before the first switch 1306 and it can be configured to control the delivery of RF electrical energy, thereby providing a multi-stage trigger assembly similar to those discussed above. In addition, other embodiments of the logic diagram 1316 can be employed that provide alternative behaviors for the device.

User-Adjustable Movement Precision

The devices and methods described herein have a number of uses in a variety of surgical procedures. Not all procedures require the same level of precision in cutting and sealing tissue. For example, when sealing large vessels surgeons often want very precise control of a cutting element. However, when sealing and transecting numerous abdominal adhesions while gaining access to a targeted organ, a surgeon may prefer a more responsive and faster moving cutting element. In certain embodiments, the devices and methods described herein can allow a user to bias a device toward greater precision or greater responsiveness.

Figure 14:
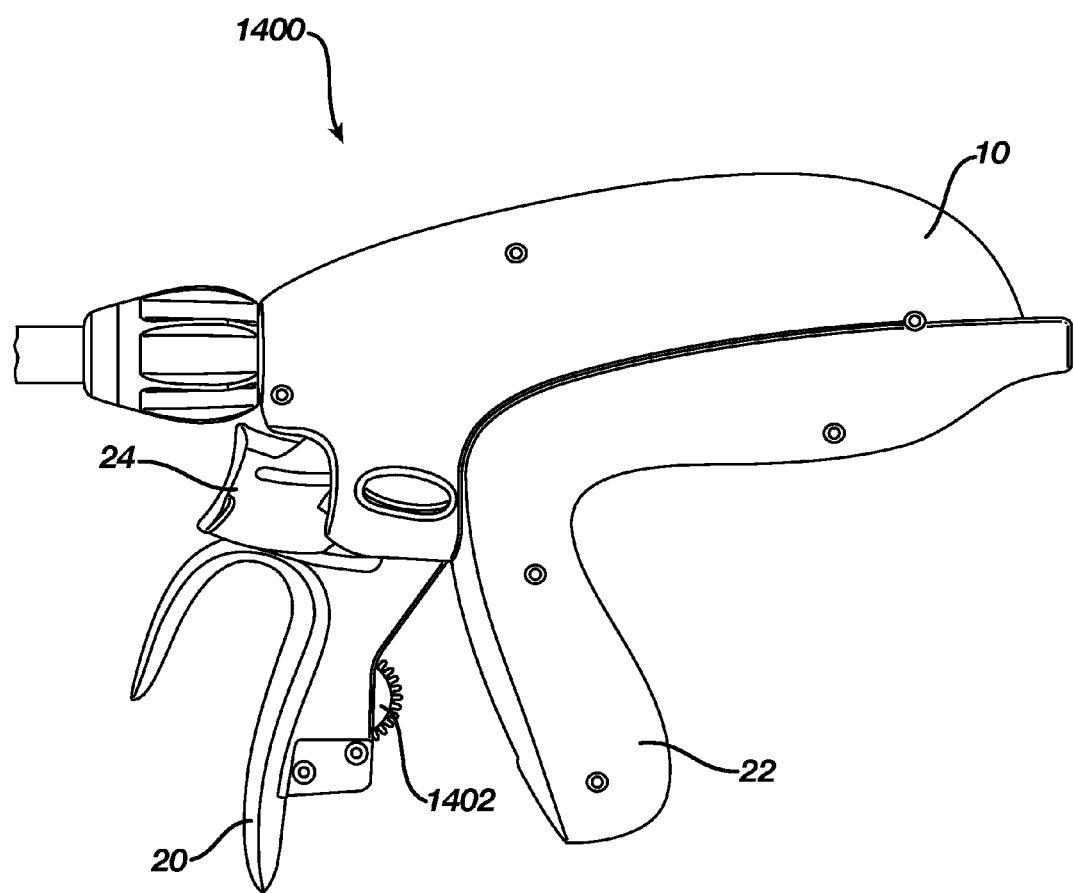
FIG. 14 is a side view illustration of one embodiment of a surgical device including a user-adjustable motor control precision selector.

FIG. 14 illustrates one embodiment of a user-adjustable device 1400, similar to the devices discussed above. The device 1400 includes a handle portion 10, a closure grip 20, a stationary grip 22, and a firing actuator 24. The device 1400 also includes a motor speed adjustment wheel 1402 located on a proximal-facing surface of the closure grip 20. The wheel can be moved between two discrete positions or simply turned to select a position in a range between two endpoints. The two discrete positions or endpoints can represent settings that bias the device 1400 toward either slower speed, more precise movement of a cutting element in the end effector of the device, or higher speed, more responsive movement of the cutting element. If the wheel can be turned to a position in the range between these two endpoints, a balance between the slower and higher speed movements can be provided. For example, in one embodiment rotating the wheel 1402 upward can increase responsiveness (i.e., increase cutting element speed), while rotating the wheel downward can increase precision (i.e., decrease cutting element speed). One of skill in the art will appreciate that there are a variety of ways to adjust the operating speed of the motor in response to the position of the wheel, including a gain adjustment of an electrical signal provided to the motor driving the cutting element.

Figure 15:
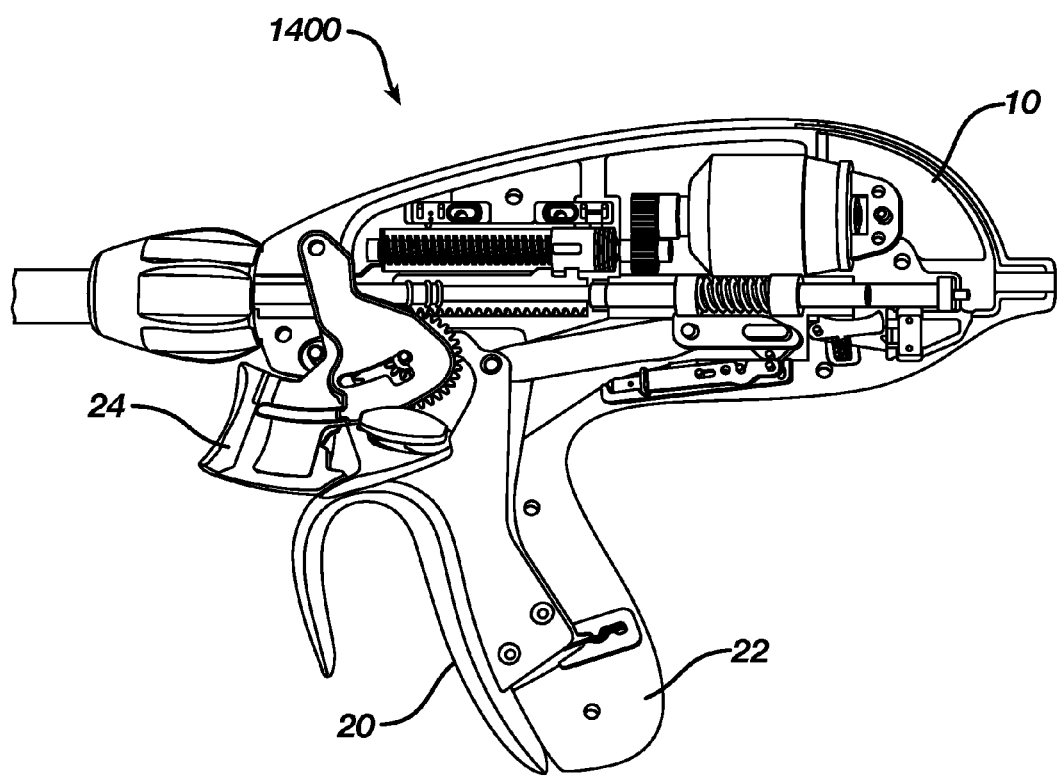
FIG. 15 is a cutaway side view illustration of the surgical device of FIG. 14 in a second position.

FIG. 15 illustrates the device of FIG. 14 when the closure grip 20 has been drawn toward the stationary grip 22 to close the jaws of the end effector and engage tissue therebetween. As shown in FIG. 15, the motor speed adjustment wheel 1402 can be inaccessible when the closure grip is in this position, as the wheel can be housed within a recess of the stationary grip 22. This configuration can provide a safety benefit of preventing unintended adjustment of motor speed when the device 1400 is engaged to tissue.

Motor Power and Speed Limits

In addition to providing a greater level of motor control and feedback to the user, a number of the deficiencies of prior art motorized surgical devices can also be addressed with motor power and speed limits that prevent a user from getting into a situation where the device is not performing as expected. For example, in a typical motorized surgical device the rotational inertia of the motor and the available motor torque represent the sum total energy available to advance a cutting element through tissue. If this total amount of energy is not adequate to advance the cutting element, e.g., if the tissue is very tough or thick, the motor can stall. Upon stalling, however, the motor will not be able to retract the cutting element and clear the stall because only the energy supplied by the motor torque (there is no rotational inertia when the motor stops to reverse direction) is available to retract the cutting element.

To address this issue, the devices and methods described herein can include a power limit when advancing a cutting element that is less than a power limit when retracting a cutting element. For example, in one embodiment, the full power of a motor may be available for retracting a cutting element, while only a portion of the full power level is available for advancing the cutting element. Such a device should always be able to clear a stall, provided that the combination of rotational inertia and the lower power level for advancing the cutting element do not exceed the full power of the motor.

Figure 16:
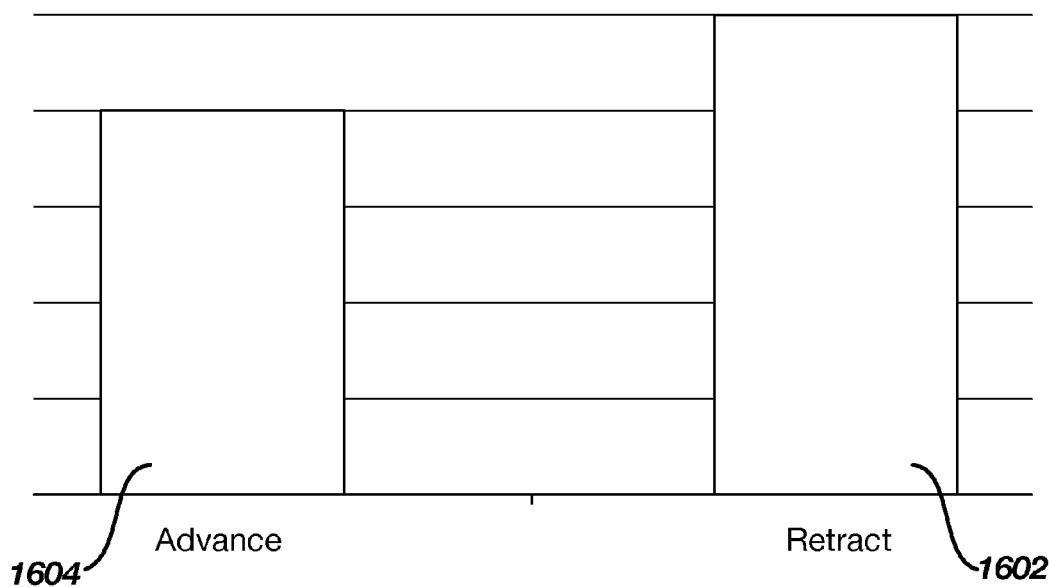
FIG. 16 is a graphical illustration of one embodiment of available motor power for advancing and retracting a cutting element.

FIG. 16A illustrates one embodiment of such a motor control scheme graphically. As shown in the figure, the motor power level available to retract a cutting element 1602 is higher than the motor power level available to advance the cutting element 1604. The exact ratio between these two power levels can be determined based on a particular motor so as to ensure that the advancing power level and rotational inertia of the motor do not exceed the retracting power level.

This motor control scheme can be implemented in motors powered through pulse-width modulation, and also in direct current (DC) motors. For example, in a DC motor the available voltage can be limited during cutting element advancement, while full voltage can be allowed during cutting element retraction.

In another embodiment, a motor control scheme can enforce a minimum speed on a motor when advancing a cutting element in order to prevent overheating of the motor during a stall. For example, motorized surgical devices often employ an "open loop" control scheme wherein a command is given but no feedback is collected to confirm successful execution of the command. This type of control scheme can work well when low power levels are required, e.g., when transecting thin tissue. When attempting to transect thicker or tougher tissue, however, a user may not command enough power from a motor to overcome the tissue. A motor stall can result and, if a user does not release the trigger (which they often may not do given the lack of feedback), the motor can overheat.

Figure 17:
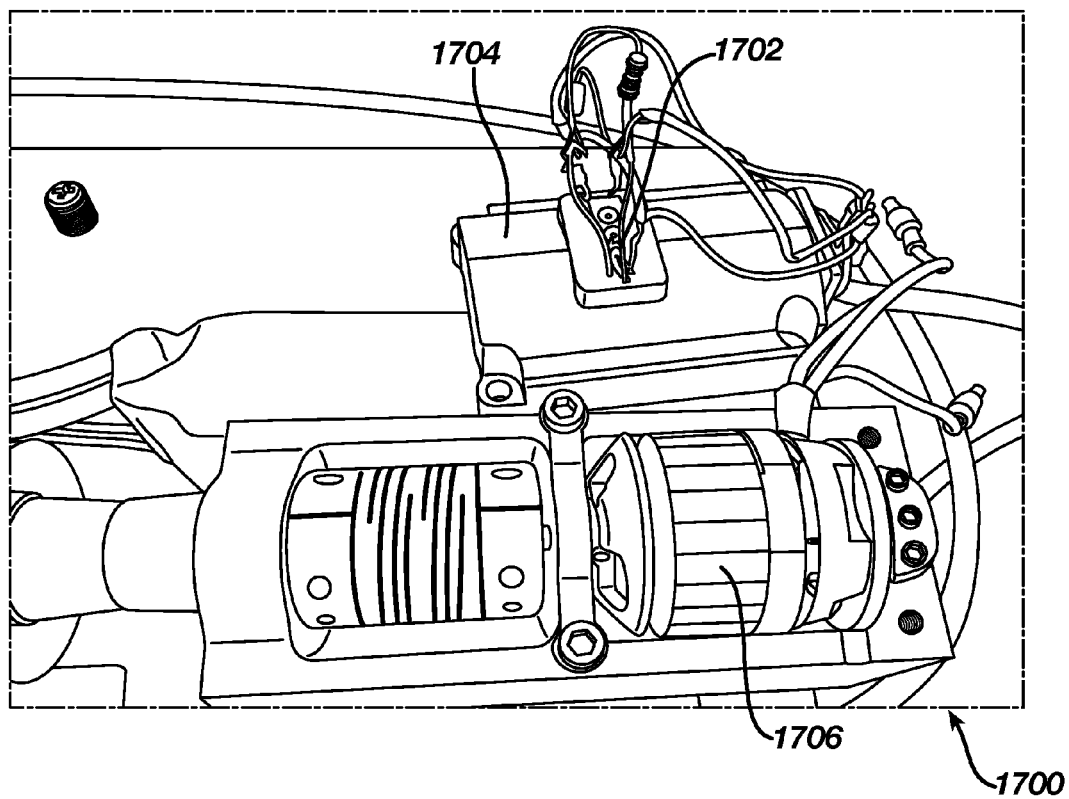
FIG. 17 is a depiction of one embodiment of surgical device including a motor speed sensor.

To prevent the development of a stall and any associated overheating of a motor, a motor control mechanism can enforce a minimum motor speed limit any time a cutting element is being advanced through tissue. Motor speed can be detected in a variety of manners, including, for example, through the use of an encoder, such as the encoder 418 discussed above. FIG. 17 illustrates one embodiment of a motor 1700 that includes an emitter/detector pair 1702 mounted in a housing 1704 of the motor (the housing 1704 is shown removed from the motor and positioned adjacent thereto). The emitter/detector pair 1702 can be positioned over a striped target 1706 placed on a rotating portion of the motor 1700. The rotational speed of the motor can be calculated by counting a number of stripes that pass in front of the emitter/detector pair 1702. An emitter/detector pair 1702 and striped target 1704 is just one example of an encoder that can be used to determine motor speed, however, and other known devices can be utilized as well. Examples include an optical encoder, rotary potentiometer, and direct sensing of motor electromagnetic force (EMF).

Note that the minimum motor speed limit need only be enforced when motor control logic indicates that the cutting element is being advanced through tissue. Referring back to FIG. 9, for example, this would be during the advancing portion 908. For other operations, there is significantly less risk of developing a stall, and a minimum motor speed limit is not necessary (though could be enforced in some embodiments).

Another problem that can be encountered with motorized surgical devices is rapid acceleration of a motor when thin tissue is transected. When motorized devices operate at low power levels, open loop control as described above can be effective because system response (e.g., acceleration of the motor and cutting element) is in a time period that allows for user reaction. The addition of increased power to transect thicker or tougher tissue, however, can produce dangerous levels of motor acceleration when the increased resistance of thicker or tougher tissue is not present.

To address this problem, a motor control mechanism can enforce a maximum motor acceleration limit to prevent rapid movements of a cutting element when encountering, for example, thin, compressible tissue. The same emitter/detector pair 1702 and striped target 1704 shown in FIG. 17 and described above can be utilized to calculate an acceleration (i.e., a rate of change in speed) of a motor 1700. The motor can then be driven to maintain the acceleration below a predetermined limit. This can allow the motor acceleration to be limited without reducing the maximum amount of power available to drive the cutting element when tough tissue is encountered. Such a limit can be effective because the presence of tough tissue can prevent the acceleration limit from being exceeded even as increasing amounts of power are applied to the motor. As noted above, alternatives to the encoder shown in FIG. 17 can be employed to determine the acceleration of a motor, including, for example, an optical encoder, rotary potentiometer, or direct sensing of motor EMF.

Still another problem encountered with motorized surgical devices is the ability to dissipate internally generated heat. Motorized surgical devices typically favor compact high power density motors that allow for the volume and weight of the device to be minimized. However, these devices often have limited opportunities to dissipate internally generated heat and have closely regulated surface temperature requirements.

To address this issue, a motor control mechanism can be configured to limit the maximum power dissipated in the motor to prevent excessive heat generation. For example, in certain embodiments a three-phase alternating current (AC) motor can be employed to drive a cutting element with a surgical device. Such a motor can be controlled through a pulse-width modulated signal. Limiting the maximum pulse width can reduce the maximum power dissipated by the motor. This can, in turn, limit the ability of the motor to rapidly accelerate a cutting element coupled thereto, while maintaining adequate power to compress and transect tissue.

Figure 18:
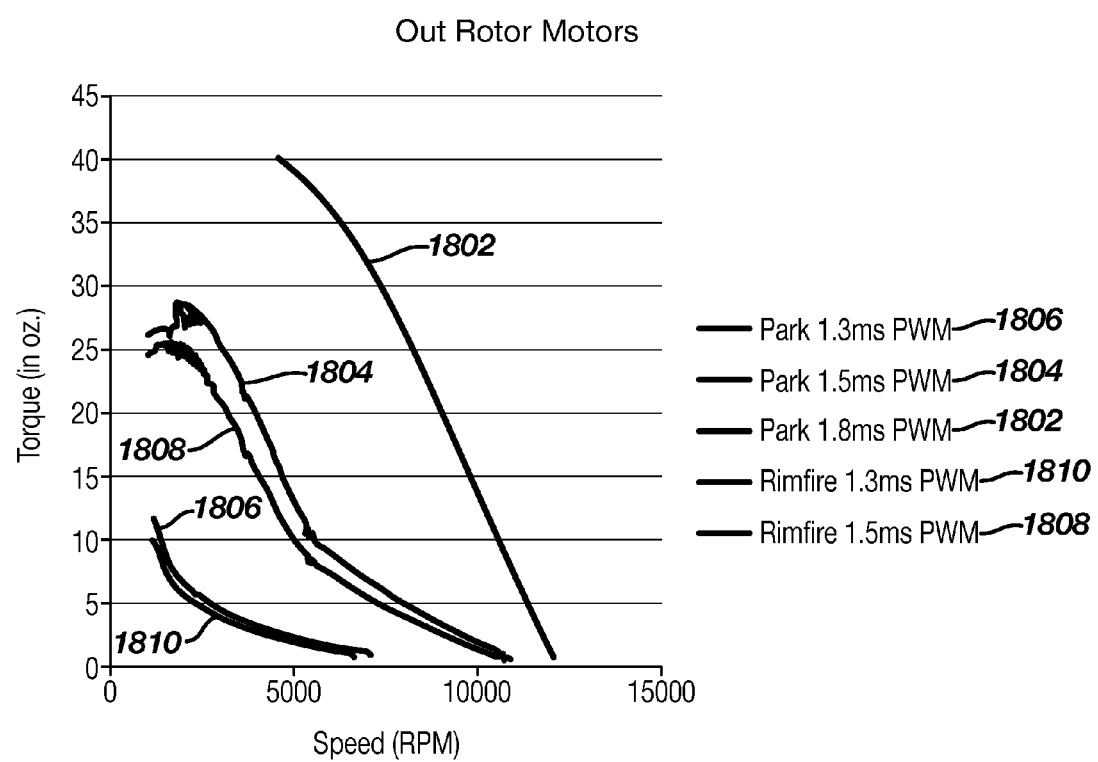
FIG. 18 is a graphical illustration of torque/speed curves for one embodiment of an electric motor in response to various pulse-width-modulated electrical signals.

FIG. 18 illustrates torque/speed curves for different pulse-width modulated control signals applied to a three-phase AC motor. In particular, FIG. 18 illustrates a first curve 1802 produced in response to a 1.8 ms pulse width, a second curve 1804 produced in response to a 1.5 ms pulse width, and a third curve 1806 produced in response to a 1.3 ms pulse width. Also shown is a fourth curve 1808 produced in response to a 1.5 ms pulse width, and a fifth curve 1810 produced in response to a 1.3 ms pulse width. As shown in the figure, the smaller pulse width signals produced lower levels of torque that would limit a motor's ability to rapidly accelerate a cutting element. Even at these lower torque levels, however, high motor speeds can be achieved that can aid in driving a cutting element through tissue.

While FIG. 18 shows torque/speed curves for a three-phase AC motor, such as the motor 606 shown in FIG. 10, alternate embodiments can apply this concept to any actuator where speed and power can be controlled through voltage or current regulation. Examples include DC motors, AC motors, linear motors, solenoids, etc. Furthermore, in some embodiments the particular pulse-width modulation utilized can change based on the position of a trigger or other firing actuator, or the pressure exerted thereon, both of which can be detected as described above. For example, a longer duration pulse-width modulation (e.g., the first curve 1802) can be utilized if a trigger is fully depressed or a pressure exerted on the trigger exceeds a threshold amount. Conversely, a shorter duration pulse-width modulation (e.g., the third curve 1806) can be utilized if a trigger is only partially depressed or a pressure exerted on the trigger is less than a threshold amount. Such an embodiment can allow for changing the pulse-width modulation based on normal or expected speed and/or torque requirements.

Mechanical Linkages for Positional Feedback

Referring back to the trigger assemblies described above, in some embodiments improved feedback and control can be provided by mechanically connecting a user input (e.g., the trigger) to a device output (e.g., the motor-driven cutting element) by way of slidably and rotationally coupled linkages. When used in combination with a motor to reduce the force necessary to drive the cutting element, users can experience increased positional and progression awareness while avoiding fatigue from actuating the device manually.

Figure 19:
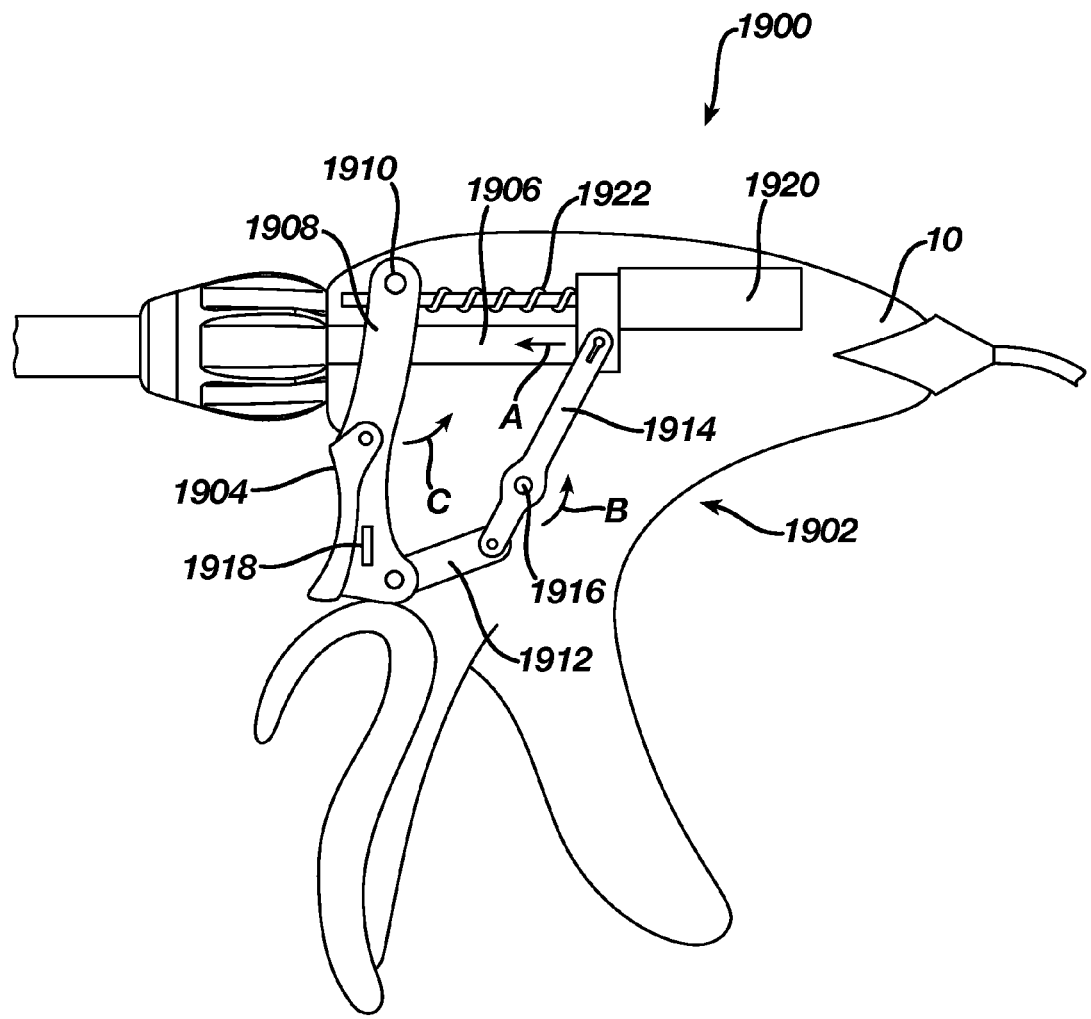
FIG. 19 is a side view illustration of one embodiment of a mechanical linkage to provide positional feedback in a powered surgical device.

FIG. 19 illustrates one embodiment of a device 1900 that includes a linkage 1902 coupling a trigger 1904 to a driving shaft 1906 that is itself coupled to a cutting element at a distal end of the device (not shown). The linkage 1902 can include an input link 1908 pivotably coupled to a handle portion 10 of the device by a pin 1910. The input link 1908 can also be pivotably coupled to an intermediate link 1912 at an end opposite pin 1908. The linkage 1902 can also include an output link 1914 that is pivotably coupled at a midpoint thereof to the handle portion 10 of the device by a pin 1916. A first end of the output link 1916 can be pivotably coupled to the intermediate link 1912 and a second end of the output link can be pivotably coupled to the driving shaft 1906.

The trigger 1904 can be pivotably coupled to the input link 1908 and can be configured to contact a switch 1918 mounted on the input link when the trigger is depressed. The switch 1918 can be electrically coupled to a controller such that actuation of the switch can trigger activation of a motor 1920 that advances the driving shaft 1906 distally using a drive screw 1922.

As a user depresses the trigger 1904 and actuates the switch 1918, the motor can begin driving the shaft 1906 distally (i.e., in the direction of arrow A) to advance the cutting element. As a result of the fact that the output link 1914 of the linkage 1902 is coupled to the shaft 1906, movement of the shaft distally can cause the output link to rotate about pin 1916 in the direction of arrow B. In addition, the input link 1908 can begin pivoting about the pin 1910 in the direction of arrow C due to the coupling of the input link and the output link 1914 via the intermediate link 1912. Accordingly, a user can directly detect the progress of the cutting operation via the trigger 1904, as the trigger will continue to depress proximally into the handle only as the shaft 1906 is driven distally. The linkage 1902 can provide direct tactile feedback and connection between the user and the cutting element, while allowing the motor 1920 to provide the necessary actuation force to drive the cutting operation.

Figure 20:
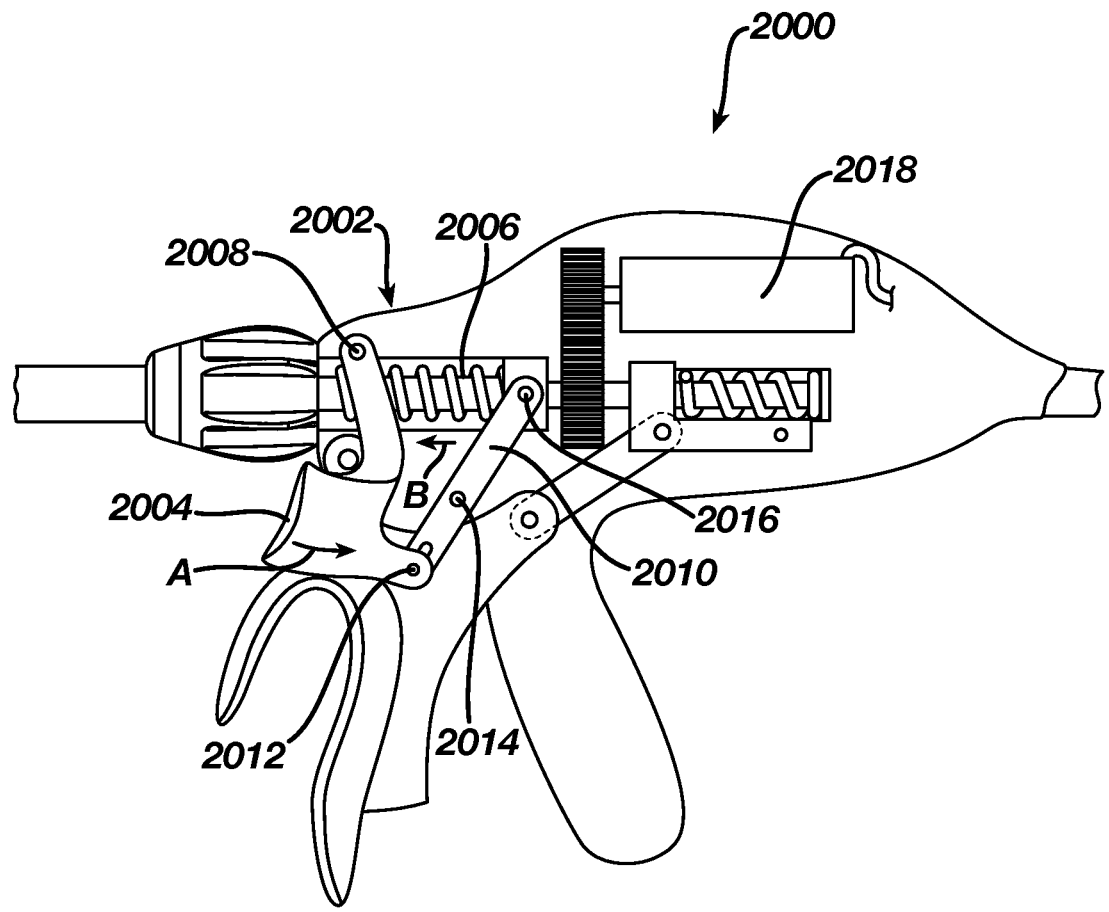
FIG. 20 is a side view illustration of an alternative embodiment of a mechanical linkage to provide positional feedback in a powered surgical device.

Other alternative embodiments of mechanical linkages are also possible. For example, the intermediate link 1912 can, in some embodiments, be eliminated and replaced by a sliding connection between the input link 1908 and the output link 1914. FIG. 20 illustrates another alternative embodiment of a linkage 2002 that couples a trigger 2004 to a driven shaft 2006. In the linkage shown in FIG. 20, the trigger 2004 can be coupled to a handle portion 10 of the device 2000 by a pin 2008. In addition, an output link 2010 can be coupled to the trigger 2004 at one end by a pin 2012, to the handle portion 10 by a pin 2014, and to the shaft 2006 by a pin 2016. As a user can depress the trigger 2004 in the direction of arrow A to activate a motor 2018 that drives the shaft 2006 in the direction of arrow B. Movement of the shaft 2006 distally can cause rotation of the output link 2010 about the pin 2014, thereby depressing the trigger 2004 further and providing feedback to the user.

Still another alternative embodiment of a mechanical linkage that connects a user input to a device output and provides positional feedback to a user is described above and shown in FIGS. 6A-6D. The mechanical linkage in that embodiment utilizes a linear rack 618 that gets driven distally by the motor 606. The motion of the rack is transferred to motion of the linkage 802 (and trigger 608) by the rotating gears 614, 616. These alternatives, and any others known to one of skill in the art to couple a user input to a device output, are all considered within the scope of the present invention. Note that any of the other components of the device shown in FIGS. 6A-6D, e.g., the trigger assembly including a strain gauge used to control a motor, can be combined with any of the other mechanical linkage embodiments described above.

Pressure Bladder as Feedback Mechanism

The embodiments disclosed above provide motor control mechanisms that can be used with motorized surgical devices. Several of these embodiments make use of a trigger assembly that is similar to those used in prior art devices, save for the fact that the trigger provides input to a motor rather than driving the cutting element directly. Such a configuration can be advantageous because the trigger architecture can be familiar for a user. In certain embodiments, however, the trigger assembly described above can be replaced with other ergonomic actuator grips because only small forces are required from a user during firing.

Figure 21A:
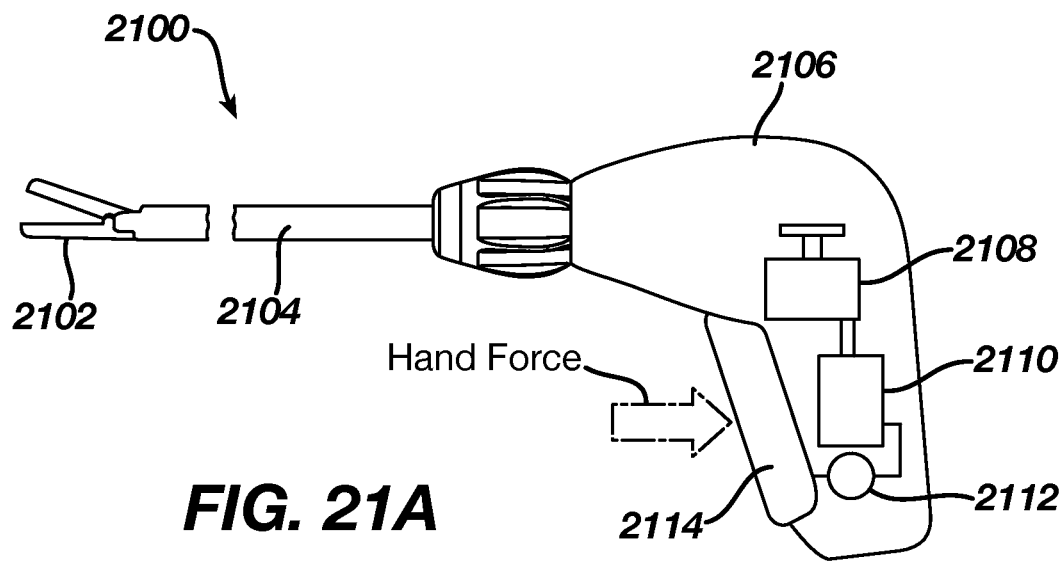
FIG. 21A is an illustration of one embodiment of a surgical device including a pressure bladder.

FIGS. 21A-21D illustrate several variations of an embodiment in which a pressure bladder is utilized to control firing rather than a more traditional trigger assembly. As shown in FIG. 21A, for example, a device 2100 can include an end effector 2102, an extension shaft 2104, and a handle portion 2106, similar to the devices described above. In addition, the device 2100 can include a motor 2108 configured to advance a cutting element positioned within or adjacent to the end effector 2102. The motor 2108 can be coupled to a digital data processor 2110 or other controller that drives the motor in response to an electrical signal output from a pressure sensor 2112. The pressure sensor 2112 can be coupled to a pressure bladder 2114 such that a pressure of a fluid (e.g., a gas or a liquid) within the bladder can be detected. The pressure bladder 2114 can be formed from a variety of materials and sizes but, in some embodiments, can be formed from a flexible fluid-impermeable material.

Figure 21B:
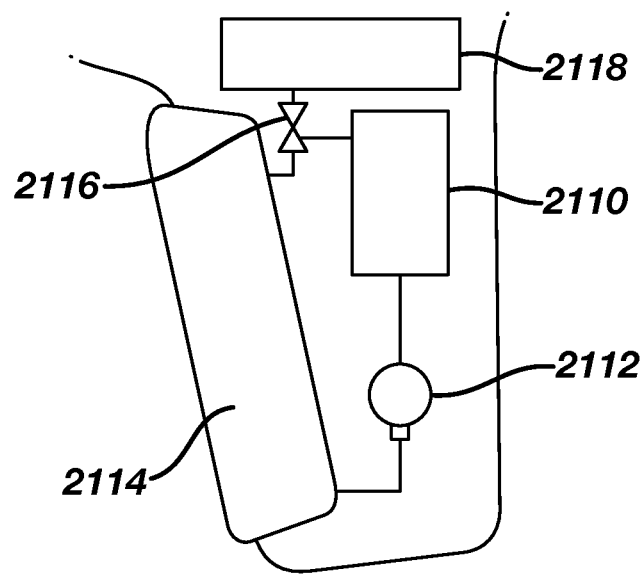
FIG. 21B is a detail view illustration of the surgical device of FIG. 21A.

In use, a user can increase their grip on the device 2100 to increase the pressure in the bladder 2114 and thereby cause the motor to drive the cutting element through tissue. In addition, in certain embodiments, sensors in the end effector 2102 can sense tissue elasticity during clamping of the end effector jaws and feed this information back to the digital data processor 2110. The processor 2110 can, in turn, increase or decrease the perceived resistance to pressure exerted on the pressure bladder 2114, e.g., by adding or removing fluid from the bladder, or changing a rate at which fluid is introduced or expelled from the bladder. One exemplary embodiment is shown in FIG. 21B, where a valve 2116 is included to control adjustment of fluid level within the pressure bladder 2114 and a separate fluid collector 2118. The valve 2116 can be controlled by the processor 2110 and a pump mechanism (not shown) can also be provided in connection with the valve 2116 to force fluid into the bladder if necessary.

Figure 21C:
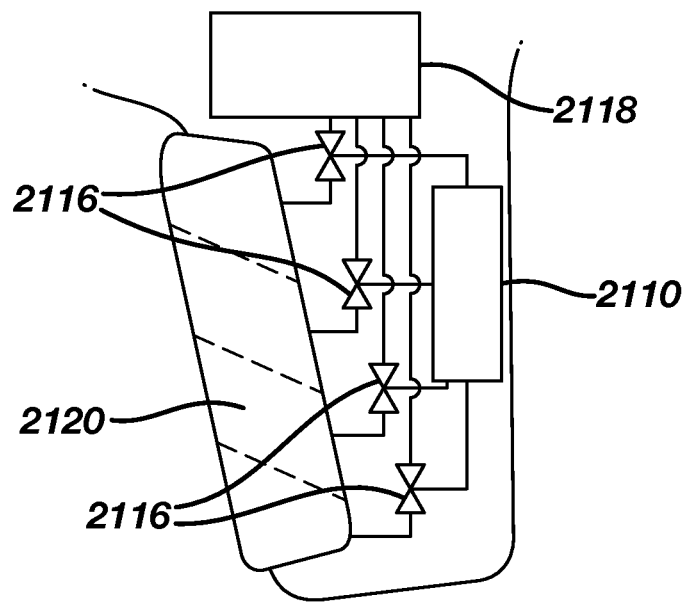
FIG. 21C is a detail view illustration of an alternative embodiment of a surgical device including a pressure bladder.

In still other embodiments, a segmented bladder 2120 can be used, as shown in FIG. 21C. Each segment of the bladder 2120 can be sealed from the others and pressure within each segment can be individually controlled by a plurality of processor-controlled valves 2116. In such a configuration, the sections of the segmented bladder 2120 can provide varying pressure to simulate the different tissue engaged by different sections of the end effector.

Figure 21D:
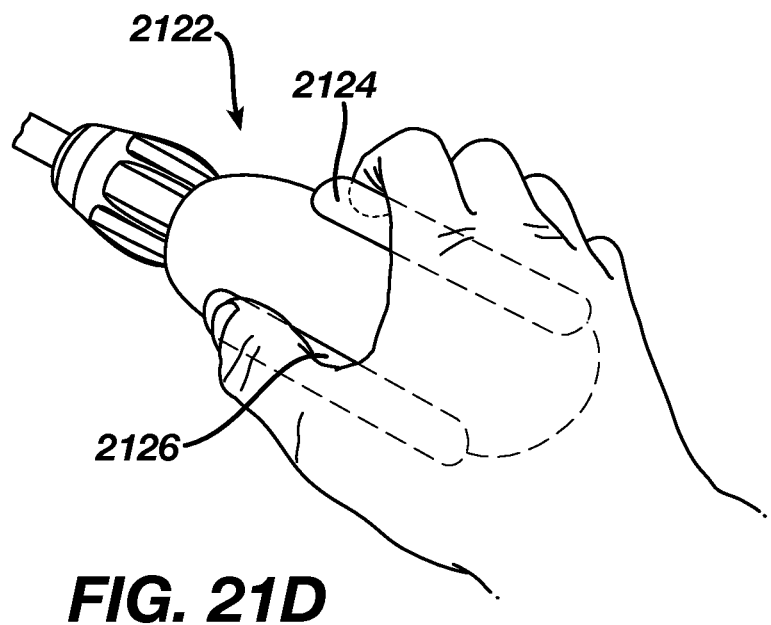
FIG. 21D is a top view illustration of an alternative embodiment of a surgical device including a pressure bladder.

In yet other embodiments, a plurality of separate bladders can be utilized in place of a single bladder or a single bladder segmented into a plurality of sections. FIG. 21D illustrates one embodiment of a device 2122 that includes a first pressure bladder 2124 on a first side of the device and a second pressure bladder 2126 on a second side of the device. One of skill in the art will appreciate that any number of pressure bladders can be utilized in a variety of different configurations on a device.

Constant Force Control Algorithm

As described above, when RF electrical energy is delivered into tissue, the tissue can reduce in size at it denatures. A force required to pass a cutting element through the tissue can also decrease as the tissue reduces during RF energy delivery, a concept commonly referred to as tissue "yielding." Experienced operators of manually-actuated surgical transection and sealing devices know to wait for tissue yielding to occur before advancing a cutting element to transect the tissue. If a user attempts to actuate a device too soon, the force required to transect the tissue can be high and the tissue may not be sealed completely, resulting in bleeding or other leakage through the cut.

The devices and methods described herein can, in some embodiments, include a motor control mechanism configured to emulate the practice of experienced users who wait for tissue yielding before advancing a cutting element. In one embodiment, this can be accomplished by including a force sensor in a mechanism that drives the cutting element (or the mechanism that closes the jaws if motor assist is used in that operation) to monitor the force required to advance the cutting element. Prior to performing a cutting operation, an initial force required to advance the cutting element a small distance (prior to cutting any tissue) can be monitored and stored as a benchmark for tissue behavior. A control algorithm can then apply a predetermined amount of power to a motor to advance the cutting element in combination with RF energy delivery and the force sensor can monitor the resistance exerted by the tissue. When a drop in the force required to deploy the cutting element is detected by the force sensor (as a result of tissue yielding from the application of RF energy), a constant force (e.g., a constant force that is greater than that applied to test tissue resistance) can be applied to the cutting element to advance it at a uniform rate of speed.

If the force required to deploy the cutting element rises above a predetermined threshold amount during the course of a cutting operation, the motor control mechanism can stop the cutting element and hold it under the predetermined amount of motor power as described above to wait for tissue yielding to occur again. Once a drop in the force required to deploy the cutting element is detected, the cutting element can again be advanced under a constant force at a uniform speed. In some embodiments, additional sensed parameters of the tissue and/or device can be included in a control algorithm. Exemplary parameters include tissue resistance/ impedance, delivered energy (which can be calculated), estimated tissue temperature, etc.

Such a control algorithm can be employed in either a "fire and forget" mode, wherein a user initializes a firing operation and the device controls the delivery of energy and deployment of the cutting element, or in a "pilot in the loop" mode, wherein the motor functions as a power-assist while giving scaled force to fire and other tactile feedback to a user. If operating in the latter mode, a scaling factor for the motor assist force can be made user-configurable, similar to the concept of motor speed adjustment discussed above. In this way, users with smaller or less powerful hands can command more gain to lower the actual force required to fire the device to some predetermined level, while a user with larger, more powerful hands can reduce the gain so as to prevent them from exerting too much force on the system, which can cause a suboptimal seal.

In some embodiments, the motor control mechanism can be configured to control the force applied to tissue to ensure it is within pre-defined or adaptively established bounds. This can prevent too much or too little pressure from being exerted on the cutting element, possibly compromising tissue sealing. For example, a motor of a device can be used to actively resist force input from a surgeon if that input would cause a cutting element to be deployed too rapidly. Conversely, the motor control mechanism can be used to prevent deployment of a cutting element before tissue has sealed properly such that a cut would bleed profusely. For example, in one embodiment a device can be configured to monitor the delivery of RF electrical energy and, if it calls below a predetermined minimum threshold, prevent further advancement of a cutting element unless a manual override is provided by a user.

A person skilled in the art will appreciate that any of the embodiments discussed above can be combined with one another in a variety of manners. Furthermore, a device could be provided that allows a user to select a particular mode that the device operates in, or what features are provided. Additionally, while the present invention can be utilized in any surgical procedure, it can have particular application in conventional minimally-invasive and open surgical procedures, as well in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Also, elements or steps from one embodiment can be readily recombined with one or more elements or steps from other embodiments. Further, one skilled in the art will appreciate further features and advantages of the invention based on the above-described embodiments. Accordingly, the invention is not to be limited by what has been particularly shown and described, except as indicated by the appended claims. Finally, all publications and references cited herein are expressly incorporated herein by reference in their entirety.

What is claimed is:

1. A surgical device, comprising:
   a proximal handle portion that includes a motor;
   a distal end effector coupled to the handle portion;
   a cutting element configured to cut a tissue engaged by the end effector, the motor being configured to supply power that moves the cutting element through the tissue; and
   a motor control mechanism configured to cause the amount of the power to dynamically change in response to a change in applied pressure of a manual user input when the cutting element is moving, and the motor control mechanism being configured to cause the amount of the power to remain constant in response to an applied pressure of the manual user input being continually applied at a steady rate when the manual user input and the cutting element are moving.

2. The device of claim 1, wherein the motor control mechanism comprises a potentiometer, the amount of the power supplied by the motor changing if a voltage of the potentiometer does not match a predetermined reference voltage, and the amount of the power supplied by the motor not changing if the voltage of the potentiometer matches the predetermined reference voltage.

3. The device of claim 1, further comprising a trigger coupled to the handle portion, the trigger being configured to be actuated by the user, the actuation of the trigger being configured to automatically actuate the motor control mechanism.

4. The device of claim 3, wherein the motor control mechanism is further configured to dynamically change the amount of the power so as to maintain a relationship between a position of the cutting element and a position of the trigger.

5. The device of claim 1, wherein when the manual user input ceases, the motor control mechanism is configured to immediately stop the motor from supplying the power.

6. The device of claim 1, wherein the motor control mechanism is configured to increase the amount of the power supplied by the motor when the amount of the power supplied by the motor falls below a predetermined threshold amount until the amount of the power supplied by the motor is at least equal to the predetermined threshold amount.

7. The device of claim 1, wherein the motor control mechanism is configured to increase the amount of power supplied by the motor in response to the manual user input increasing in pressure.

8. The device of claim 1, further comprising a feedback mechanism configured to provide a tactile feedback to the user, the tactile feedback being representative of the amount of the power being supplied by the motor.

9. A surgical method, comprising:
engaging a tissue with a distal end effector of a surgical device, the surgical device comprising a cutting element configured to cut a tissue engaged by the end effector, a proximal handle portion that includes a motor configured to supply power that moves the cutting element through the tissue, the distal end effector coupled to the handle portion, and a motor control mechanism configured to cause the amount of the power to dynamically change in response to a change in applied pressure of a manual user input when the cutting element is moving, and the motor control mechanism being configured to cause the amount of the power to remain constant in response to an applied pressure of the manual user input being continually applied at a steady rate when the manual user input and the cutting element are moving;
causing the motor of the device to supply power to the cutting element of the device such that the cutting element moves through the tissue so as to cut the tissue; and
when the cutting element is moving, detecting a change in a magnitude of a manual user force being applied to the manual user input, and causing an amount of the power supplied by the motor to dynamically change in response to the detected change.

10. The method of claim 9, providing a tactile feedback to the user via the device, the tactile feedback indicating the amount of the power.

* * * * *